(12) United States Patent
Shalek et al.

(10) Patent No.: US 11,643,669 B2
(45) Date of Patent: May 9, 2023

(54) CRISPR MEDIATED RECORDING OF CELLULAR EVENTS

(71) Applicant: Massachusetts Institute of Technology, Cambridge, MA (US)

(72) Inventors: Alexander K. Shalek, Cambridge, MA (US); Alethe Gaillard De Saint Germain, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 403 days.

(21) Appl. No.: 15/837,835

(22) Filed: Dec. 11, 2017

(65) Prior Publication Data

US 2019/0055583 A1    Feb. 21, 2019

Related U.S. Application Data

(63) Continuation-in-part of application No. PCT/US2016/038205, filed on Jun. 17, 2016.

(60) Provisional application No. 62/180,652, filed on Jun. 17, 2015.

(51) Int. Cl.
| | | |
|---|---|---|
| C12N 15/90 | (2006.01) | |
| C12Q 1/68 | (2018.01) | |
| C12N 15/11 | (2006.01) | |
| C12N 15/85 | (2006.01) | |
| C12N 15/10 | (2006.01) | |
| C12N 9/22 | (2006.01) | |
| C12Q 1/6876 | (2018.01) | |

(52) U.S. Cl.
CPC ............ *C12N 15/907* (2013.01); *C12N 9/22* (2013.01); *C12N 15/102* (2013.01); *C12N 15/11* (2013.01); *C12N 15/111* (2013.01); *C12N 15/85* (2013.01); *C12Q 1/68* (2013.01); *C12Q 1/6876* (2013.01); *C12N 2310/20* (2017.05); *C12N 2320/00* (2013.01); *C12N 2320/10* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 4,186,183 A | 1/1980 | Alving et al. | |
| 4,217,344 A | 8/1980 | Handjani et al. | |
| 4,235,871 A | 11/1980 | Papahadjopoulos et al. | |
| 4,261,975 A | 4/1981 | Fullerton et al. | |
| 4,485,054 A | 11/1984 | Mezei et al. | |
| 4,774,085 A | 9/1988 | Fidler | |
| 4,797,368 A | 1/1989 | Carter et al. | |
| 4,837,028 A | 6/1989 | Allen | |
| 4,873,316 A | 10/1989 | Meade et al. | |
| 4,897,355 A | 1/1990 | Eppstein et al. | |
| 4,946,787 A | 8/1990 | Eppstein et al. | |
| 5,049,386 A | 9/1991 | Eppstein et al. | |
| 5,173,414 A | 12/1992 | Lebkowski et al. | |
| 6,603,061 B1 | 8/2003 | Armstrong et al. | |
| 6,750,059 B1 | 6/2004 | Blakesley et al. | |
| 7,708,949 B2 | 5/2010 | Stone et al. | |
| 7,776,321 B2 | 8/2010 | Cascalho et al. | |
| 7,868,149 B2 | 1/2011 | Boukharov et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |

(Continued)

FOREIGN PATENT DOCUMENTS

| | | |
|---|---|---|
| EP | 0264166 A1 | 4/1988 |
| EP | 2764103 A2 | 8/2014 |

(Continued)

OTHER PUBLICATIONS

Schmidt et al., "CRISPR genome engineering and viral gene delivery: A case of mutual attraction" 10 Biotechnology Journal 258-272 (Year: 2015).*

F. Farzadfard, et al., Genomically Encoded Analog Memory with Precise In Vivo DNA Writing in Living Cell Populations, Science (Nov. 14, 2014) vol. 346, No. 6211, p. 1256272-1256272-8.

A. Friedland, et al., Synthetic Gene Networks That Count, Science, American Association for the Advancement of Science, US (May 29, 2009) vol. 324, No. 5931, p. 1199-1202.

Siuti Piro, et al., Synthetic Circuits integrating Logic and Memory in Living Cells, Nature Biotechnology (Feb. 10, 2013) vol. 31, No. 5, p. 448-452.

(Continued)

*Primary Examiner* — Nancy J Leith
(74) *Attorney, Agent, or Firm* — F. Brent Nix, Esq.; Johnson, Marcou, Isaacs & Nix, LLC

(57) ABSTRACT

The present invention relates to systems and methods for recording and assaying cellular events, in particular gene expression. The invention provides hereto a method of determining a cellular event of interest in a cell comprising providing a cell comprising a CRISPR-Cas system, wherein the CRISPR-Cas system comprises a guide RNA that targets a selected DNA sequence and a Cas protein capable of modifying the selected DNA sequence; whereby a nucleic acid molecule encoding at least one of the guide RNA or Cas protein is operably connected in the cell with a regulatory element comprising a promoter responsive to the cellular event, and whereby expression of at least one CRISPR-Cas system component is driven by the promoter; and determining cellular event of interest based on detection of the modification of the selected DNA sequence.

31 Claims, 11 Drawing Sheets

Specification includes a Sequence Listing.

(56) References Cited

U.S. PATENT DOCUMENTS

| | | |
|---|---|---|
| 8,999,641 B2 | 4/2015 | Zhang et al. |
| 2004/0171156 A1 | 9/2004 | Hartley et al. |
| 2004/0242517 A1 | 12/2004 | Cascalho et al. |
| 2006/0163385 A1 | 7/2006 | Link et al. |
| 2007/0003442 A1 | 1/2007 | Link et al. |
| 2007/0184489 A1 | 8/2007 | Griffiths et al. |
| 2007/0195127 A1 | 8/2007 | Ahn et al. |
| 2008/0003142 A1 | 1/2008 | Link et al. |
| 2008/0014589 A1 | 1/2008 | Link et al. |
| 2009/0005254 A1 | 1/2009 | Griffiths et al. |
| 2009/0100536 A1 | 4/2009 | Adams et al. |
| 2009/0131543 A1 | 5/2009 | Weitz et al. |
| 2011/0027239 A1 | 2/2011 | Paek |
| 2011/0059502 A1 | 3/2011 | Chalasani |
| 2011/0265198 A1 | 10/2011 | Gregory et al. |
| 2012/0003201 A1 | 1/2012 | Nicholas et al. |
| 2012/0017290 A1 | 1/2012 | Cui et al. |
| 2012/0219947 A1 | 8/2012 | Yurkovetsky et al. |
| 2013/0236946 A1 | 9/2013 | Gouble |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0256595 A1 | 9/2014 | Link et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0133315 A1* | 5/2015 | Jacobson ............... C12N 15/70 506/2 |
| 2015/0225801 A1* | 8/2015 | Cai ..................... C12Q 1/6888 506/9 |
| 2018/0010134 A1 | 1/2018 | Sharp et al. |

FOREIGN PATENT DOCUMENTS

| | | |
|---|---|---|
| EP | 2771468 A1 | 9/2014 |
| EP | 2784162 A1 | 10/2014 |
| WO | 9116024 A1 | 10/1991 |
| WO | 9117424 A1 | 11/1991 |
| WO | 9324641 A2 | 12/1993 |
| WO | 9426877 A1 | 11/1994 |
| WO | 9639154 A1 | 12/1996 |
| WO | 9703211 A1 | 1/1997 |
| WO | 0189788 A2 | 11/2001 |
| WO | 2004002627 A2 | 1/2004 |
| WO | 2004091763 A2 | 10/2004 |
| WO | 2005021151 A1 | 3/2005 |
| WO | 2006040551 A2 | 4/2006 |
| WO | 2006040554 A1 | 4/2006 |
| WO | 2006096571 A2 | 9/2006 |
| WO | 2007081385 A2 | 7/2007 |
| WO | 2007089541 A2 | 8/2007 |
| WO | 2007133710 A2 | 11/2007 |
| WO | 2008063227 A2 | 5/2008 |
| WO | 2011028929 A3 | 3/2011 |
| WO | 2011079176 A2 | 6/2011 |
| WO | 2013138585 A1 | 9/2013 |
| WO | 2014018423 A2 | 1/2014 |
| WO | 2014047561 A1 | 3/2014 |
| WO | 2014085802 A1 | 6/2014 |
| WO | 2014093595 A1 | 6/2014 |
| WO | 2014093622 A2 | 6/2014 |
| WO | 2014093635 A1 | 6/2014 |
| WO | 2014093655 A2 | 6/2014 |
| WO | 2014093661 A2 | 6/2014 |
| WO | 2014093694 A1 | 6/2014 |
| WO | 2014093701 A1 | 6/2014 |
| WO | 2014093709 A1 | 6/2014 |
| WO | 2014093712 A1 | 6/2014 |
| WO | 2014093718 A1 | 6/2014 |
| WO | 2014143381 A1 | 9/2014 |
| WO | 2014204723 A1 | 12/2014 |
| WO | 2014204724 A1 | 12/2014 |
| WO | 2014204725 A1 | 12/2014 |
| WO | 2014204726 A1 | 12/2014 |
| WO | 2014204727 A1 | 12/2014 |
| WO | 2014204728 A1 | 12/2014 |
| WO | 2014204729 A1 | 12/2014 |
| WO | 2014210353 A2 | 12/2014 |
| WO | 2015065964 A1 | 5/2015 |
| WO | 2016040476 A1 | 3/2016 |
| WO | 2016049024 A2 | 3/2016 |
| WO | 2016049258 A2 | 3/2016 |
| WO | 2016094874 A1 | 6/2016 |
| WO | 2016094880 A1 | 6/2016 |
| WO | 2016205728 A1 | 12/2016 |

OTHER PUBLICATIONS

C. M. Ajo-Franklin, et al., Rational Design of Memory in Eukaryotic Ceils, Genes & Development (Sep. 15, 2007) vol. 21, No. 18, p. 2271-2276.

S.D. Perli, et al., Continuous Genetic Recording with Self-Targeting CRISPR-Cas in Human Cells, Science (Aug. 18, 2016) vol. 353, No. 6304. p. aag0511-aag0511-10.

International Search Reported dated Oct. 24, 2016 for PCT/US2016/038205.

Massachusetts Institute of Technology, "International Preliminary Report on Patentability issued in International Application No. PCT/US2016/038205", dated Dec. 28, 2017, 10 pages.

Chen, et al., "Genome-Wide CRISPR Screen in a Mouse Model of Tumor Growth and Metastasis", Cell, vol. 160, No. 6, Mar. 12, 2015, 28 pages.

Dong, et al., "Multiplex Genome Engineering Using CRISPR/Cas Systems", Science, vol. 339, No. 6121, Feb. 15, 2013, 819-823.

Doench, et al., "Rational Design of Highly Active SgRNAs for CRISPR-Cas9-Mediated Gene Inactivation", Nature Biotechnology, vol. 32, No. 12, Dec. 2014, 17 pages.

Gao, et al., "Self-Processing of Ribozyme-Flanked RNAs into Guide RNAs in Vitro and in Vivo for CRISPR-Mediated Genome Editing", Plant biology, vol. 56, 2014, 343-349.

Gilbert, et al., "Genome-Scale CRISPR-Mediated Control of Gene Repression and Activation", Cell, vol. 159, Oct. 23, 2014, 647-661.

Hsu, et al., "Development and Applications of CRISPR-Cas9 for Genome Engineering", Cell, vol. 157, No. 6, Jun. 5, 2014, 34 pages.

Hsu, et al., "DNA Targeting Specificity of RNA-Guided Cas9 Nucleases", Nature Biotechnology, vol. 31, No. 9, Sep. 2013, 17 pages.

Jiang, et al., "RNA-Guided Editing of Bacterial Genomes Using CRISPR-Cas Systems", Nature Biotechnology, vol. 31, No. 3, Mar. 2013, 9 pages.

Koike-Yusa, et al., "Genome-Wide Recessive Genetic Screening in Mammalian Cells with a Lentiviral CRISPR-Guide RNA Library", Nature Biotechnology, vol. 32, 2014, 267-273.

Konermann, et al., "Genome-Scale Transcriptional Activation by an Engineered CRISPR-Cas9 Complex", Nature, vol. 517, No. 7536, Jan. 29, 2015, 18 pages.

Konermann, et al., "Optical Control of Mammalian Endogenous Transcription and Epigenetic States", Nature, vol. 500, No. 7463, Aug. 22, 2013, 18 pages.

Nishimasu, et al., "Crystal Structure of Cas9 in Complex with Guide RNA and Target DNA", Cell, vol. 156, No. 5, Feb. 27, 2014, 25 pages.

Nishimasu, et al., "Crystal Structure of *Staphylococcus aureus* Cas9", Cell, vol. 162, No. 5, Aug. 27, 2015, 24 pages.

(56) References Cited

OTHER PUBLICATIONS

Nissim, et al., "Multiplexed and Programmable Regulation of Gene Networks with an Integrated RNA and CRISPR/Cas Toolkit in Human Cells", Molecular Cellular Biology, vol. 54 May 22, 2014, pp. 698-710.

Parnas, et al., "A Genome-Wide CRISPR Screen in Primary Immune Cells to Dissect Regulatory Networks", Cell, vol. 162, No. 3, Jul. 30, 2015, 24 pages.

Platt, et al., "CRISPR-Cas9 Knockin Mice for Genome Editing and Cancer Modeling", Cell, vol. 159, No. 2, Oct. 39, 2014, 31 pages.

Ramanan, et al., "CRISPR/Cas9 Cleavage of Viral DNA Efficiently Suppresses Hepatitis B Virus", Scientific Reports, vol. 5, No. 10833, Jun. 2, 2015, 9 pages.

Ran, et al., "Double Nicking by RNA-Guided CRISPR Cas9 for Enhanced Genome Editing Specificity", Cell, vol. 154, No. 6, Sep. 12, 2013, 19 pages.

Ran, et al., "Genome Engineering Using the CRISPR-Cas9 System", Nature Protocols, vol. 8, No. 11, Nov. 2013, 49 pages.

Ran, et al., "In Vivo Genome Editing using Staphylococcus Aureus Cas9", Nature, vol. 520, No. 7546, Apr. 9, 2015, 30 pages.

Shalem, et al., "Genome-Scale CRISPR-Cas9 Knockout Screening in Human Cells", Science, vol. 343, No. 6166, Jan. 3, 2014, 10 pages.

Shalem, et al., "High-Throughput Functional Genomics Using CRISPR-Cas9", Nature Reviews Genetics, vol. 16, No. 5, May 2015, 28 pages.

Shmakov, et al., "Discovery and Functional Characterization of Diverse Class 2 CRISPR-Cas Systems", Molecular Cell, vol. 60, No. 3, Nov. 5, 2015, 23 pages.

Swiech, et al., "In Vivo Interrogation of Gene Function in the Mammalian Brain Using CRISPR-Cas9", Nature Biotechnology, vol. 33, No. 1, Jan. 2015, 9 pages.

Tsai, et al., "Dimeric CRISPR RNA-Guided FokI Nucleases for Highly Specific Genome Editing", Nature Biotechnology, vol. 32, No. 6, Jun. 2014, 569-577.

Wang, et al., "Genetic Screens in Human Cells Using the CRISPR/Cas9 System", Science, vol. 343, No. 6166, Jan. 3, 2014, 12 pages.

Wang, et al., "One-Step Generation of Mice Carrying Mutations in Multiple Genes by CRISPR/Cas-Mediated Genome Engineering", Cell, vol. 153, No. 4, May 9, 2013, 13 pages.

Wu, et al., "Genome-Wide Binding of the CRISPR Endonuclease Cas9 in Mammalian Cells", Nature Biotechnology, vol. 32, No. 7, Jul. 2014, 20 pages.

Xu, et al., "Sequence Determinants of Improved CRISPR SgRNA Design", Genome Research, vol. 25, No. 8, Aug. 2015, 1147-1157.

Xue, et al., "CRISPR-Mediated Direct Mutation of Cancer Genes in the Mouse Liver", Nature, vol. 514, No. 7522, Oct. 16, 2014, 380-384.

Zetche, et al., "A Split Cas9 Architecture for Inducible Genome Editing and Transcription Modulation", Nature Biotechnology, vol. 33, No. 2, Feb. 2015, 6 pages.

Zetsche, et al., "Cpf1 is a Single RNA-Guided Endonuclease of a Class 2 CRISPR-Cas System", Cell, vol. 163, No. 3, Oct. 22, 2015, 14 pages.

\* cited by examiner

Decision to produce guide RNAs may depend on a complex combination of factors

Figure 7. Guide may target Cas9 itself (self inactivation), whether endogenously or exogenously expressed Presence of guide RNAs and Cas9 causes alteration to a DNA template which can be read via sequencing. If the guide RNA or Cas9 is driven by a specific event (e.g., change in a protein's level), the alteration actually reports previous cellular activity

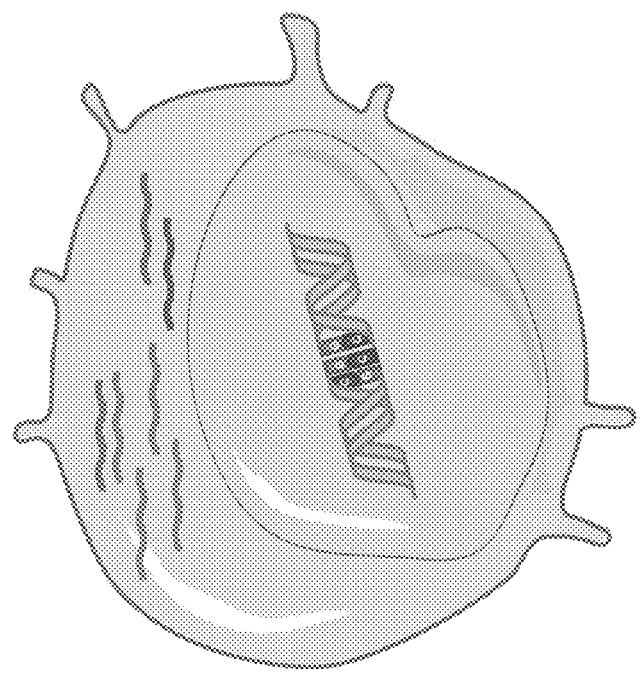

Vs.

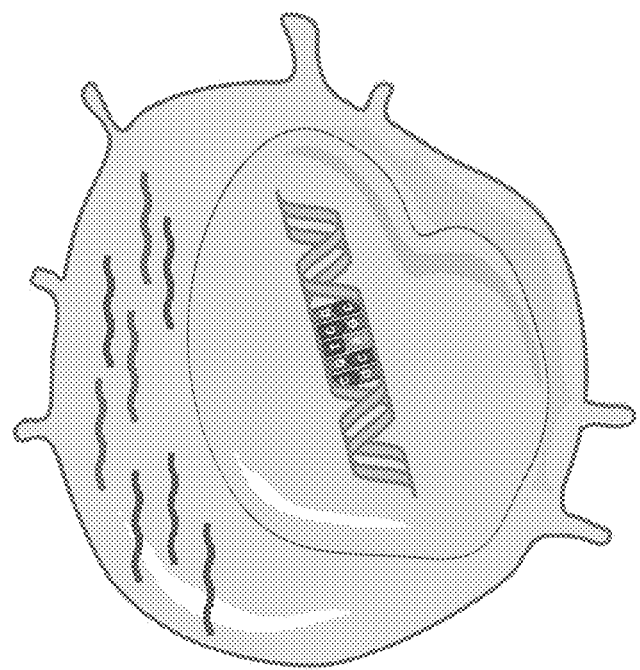

Cellular DNA (endogenous or exogenous) and RNA can be coamplified from the same single cell. If changes to the DNA are driven by cellular events through guide RNAs and/or Cas9, differences in DNA will reflect differences in cellular events; this can be used to seperate cells for downstream analyses (e.g., cells in which the event occured vs those in which it did not occur).

Figure 9

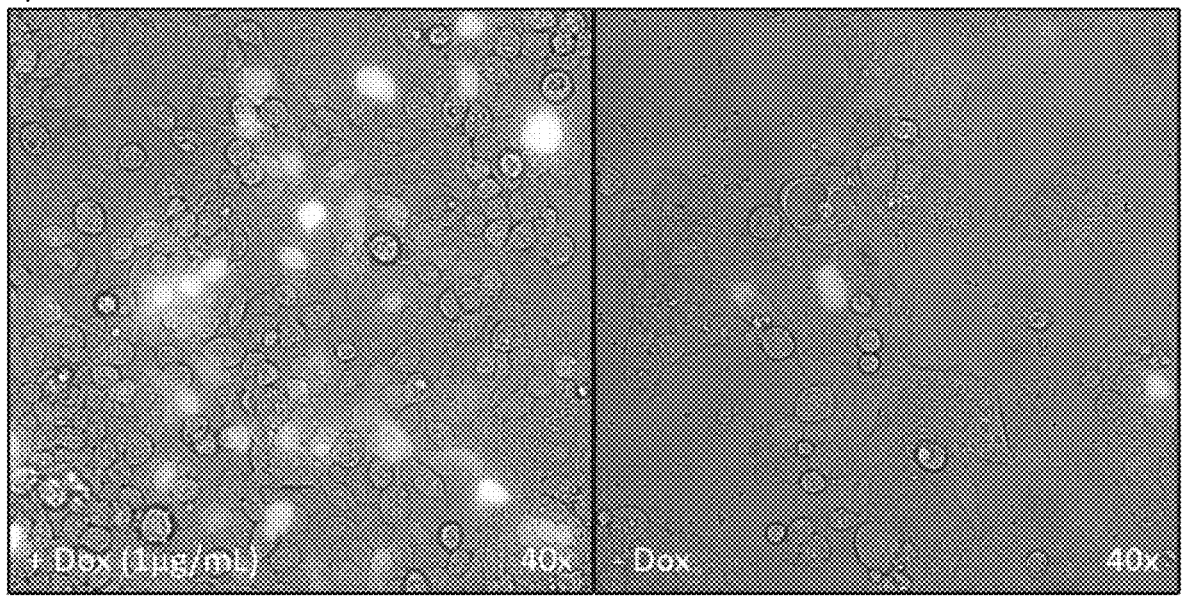
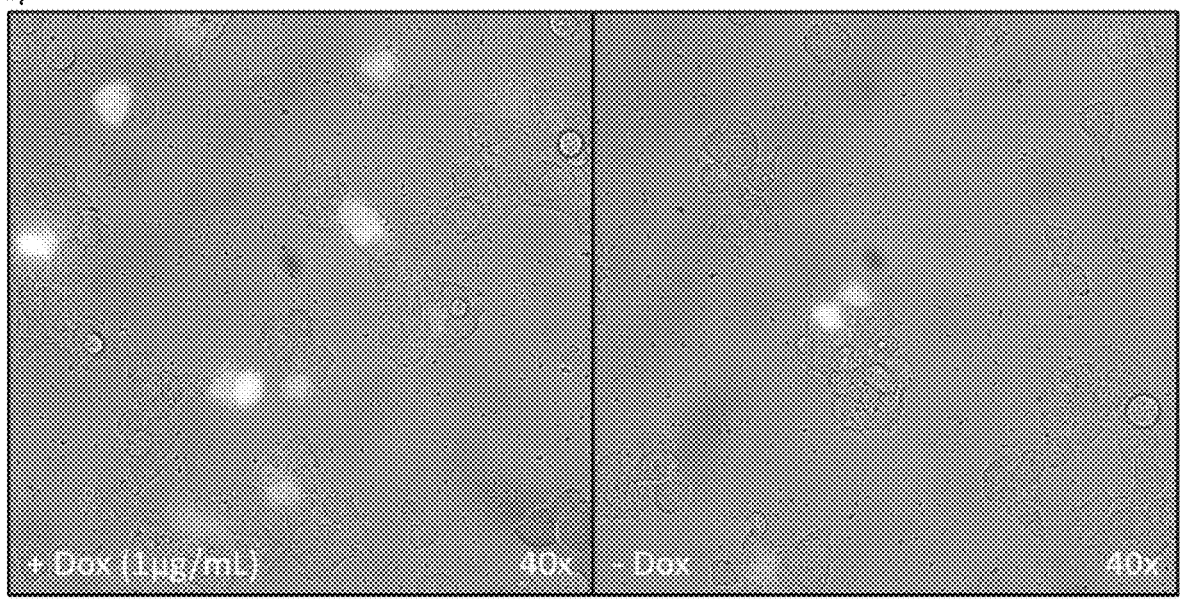
Figure 11

CRISPR MEDIATED RECORDING OF CELLULAR EVENTS

RELATED APPLICATIONS AND INCORPORATION BY REFERENCE

This application is a continuation-in-part of international patent application Serial No. PCT/US2016/038205 filed Jun. 17, 2016, which published as PCT Publication No. WO2016/205728 on Dec. 22, 2016 and which claims priority and benefit of U.S. provisional application Ser. No. 62/180,652 filed Jun. 17, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Sep. 9, 2016, is named 44790.99.2065_SL.txt and is 13,168 bytes in size.

FIELD OF THE INVENTION

The present invention relates to assaying cellular history. The present invention provides hereto methods and systems for recording cellular events which can be read out.

BACKGROUND OF THE INVENTION

The recent emergence of single cell genomic approaches, and especially single-cell RNA-seq, opens a new path for unbiased molecular profiling of individual cells from which we can identify cell states and their associated signatures (Shalek et al, Nature, 2013; Shalek et al, Nature, 2014; Patel et al, Science, 2014). Nevertheless, this approach is fundamentally limited in that it only affords a single, detailed snapshot of the cell (we need to lyse a cell to sequence all of its RNA), obfuscating the trajectory by which it arrived at the assayed state.

Ideally, one would couple temporally obtained information ('metadata') with genomic profiles (e.g. single cell genomic profiles), whether obtained from health or diseased cells, as a means of more thoroughly dissecting salient cellular circuitry and their molecular drivers (i.e., to determine why a particular measured behavior occurred: was it the level of a transcription factor? a molecule in the environment? etc.). Being able to assay a cell's history would also be of great value for tying measured genomic profiles to other sources of information.

There is a need in the art for providing methods and systems which allow recording cellular history and cellular events, being it on a single cell level or alternatively on the level of cell populations or organs, in order to provide a better understanding of how and why a particular cell (population) arrived at a specific state or endpoint.

Citation or identification of any document in this application is not an admission that such document is available as prior art to the present invention.

SUMMARY OF THE INVENTION

CRISPR (Clustered Regularly Interspaced Short Palindromic Repeats) Cas9-mediated gene disruption has been widely used in generating loss-of-function mutations in diverse organisms including mammals (Cong et al., 2013; Mali et al., 2013) (reviewed in (Hsu et al., 2014)). Cas9-based knockout screens have been applied in identifying essential genes and genes involved in drug resistance in various cell lines (Koike-Yusa et al., 2014; Shalem et al., 2014; Wang et al., 2014).

The present inventors have in an unprecedented way adapted the use of the CRISPR/Cas system in that rather than using the system to modify genomic content as a means of inducing or testing a specific phenotype (i.e., what is the impact of knocking out a specific gene), the system according to the present invention is used as a means of recording specific cellular events.

Hereto, guide RNA(s) are designed to target a specific DNA sequence. One or more of the components of the CRISPR/Cas system (e.g. guide RNA, Cas, or both) are introduced in a cell (population) and placed under control of (a) gene-specific promoter(s), such as for instance a promoter of a transcription factor. Then only in the presence of that factor (i.e. when that factor is expressed) the CRISPR/Cas component(s) are expressed and the specific DNA target sequence is edited (generate a permanent "yes" as a DNA modification by the action of the CRISPR/Cas system). By examining the cell's specific DNA target sequence, one is able to determine if and which cells had expressed Gata3 (by looking for editing) and which had not. In this way for instance the impact of a particular factor's presence on cellular phenotype can be assayed.

In addition, one or more of the CRISPR/Cas system components can be placed under control of an inducible promoter, which allows to specifically examine whether the factor was active during a certain time window (i.e., when the inducer was provided). By daisy chaining a series of these 'yes' or 'no' assays together, a "cellular questionnaire" can be built. Furthermore, specific design of the guide RNA(s), such as for instance overlapping target sequences, allows to determine temporal ordering (e.g., one cut site driven by the CRISPR system having a guide RNA or Cas under control of promoter X destroys the cut site driven by the CRISPR system having a guide RNA or Cas under control of promoter Y), activity during different windows (two different inducers), absence of a factor (a repressor during induction), the level of factors in the microenvironment, and more. This questionnaire can for instance be written in the form of a plasmid or a series of native genomic loci.

The present invention therefore allows expression profiling over time. Rather than to provide momentary information at the time of assaying, the present invention allows to capture and record cellular events during certain time frames, i.e. the present invention allows to capture and record if and when selected genes have been expressed at time point prior to and up to the moment of assaying.

Accordingly, in an aspect, the invention relates to a method for encoding, capturing, or recording cellular events or cellular history in a cell comprising providing a cell comprising a CRISPR-Cas system, said CRISPR-Cas system comprising a guide RNA that targets a selected recorder DNA sequence and a Cas protein capable of modifying the selected DNA sequence; whereby a nucleic acid molecule encoding at least one of said guide RNA or Cas protein is operably connected in the cell with a regulatory element comprising a promoter that is activated in parallel to the cellular event or as a consequence of the cellular event, and whereby expression of at least one CRISPR-Cas system component is driven by the promoter; thereby recording cellular events or cellular history as modification of said selected DNA sequence. The cellular event may be a change in expression of a gene of interest, a change in level of a protein of interest, a change in the level of an intracellular molecule, a change in a posttranslational modification, a change in the activity of a molecule of interest, a change in microenvironment, exposure to a factor of interest, activation of a transcription factor, deactivation of a transcriptional repressor, recruitment of a transcription factor, activation of a signal transduction pathway, or remodeling of chromatin. The promoter may be a promoter of a gene of interest. The promoter may be responsive to a specific transcription factor. The transcription factor may be recruited to the promoter as a result of activation of a signal transduction pathway. The promoter may be responsive to a signaling molecule. The promoter may be responsive to a nuclear receptor. Exposure to a factor of interest may comprise exposure to a chemical, biochemical, signaling molecule, or pathogen. Many promoters as known in the art can be used that are responsive to an exogenous agent or an intracellular event. The present invention can be used for determining that a cell of interest has come in contact with an extracellular agent or an intracellular event occurred. A change in activity can include changes in protein or RNA (universal or isoform specific) levels (up or down), changes in post-translational modifications (e.g., phosphorylation), changes in exposure to an endogenous factor (e.g., a chemical), changes in microenvironment (e.g., cytokine exposure) The present invention provides methods of determining changes in the activity of a factor of interest in a cell (intracellular) and methods of determining the exposure of cell to a factor of interest (e.g., a pathogen or chemical, extracellular).

In an alternative aspect, the invention relates to a method of determining expression of a gene of interest in a cell comprising providing a cell comprising a CRISPR-Cas system, said CRISPR-Cas system comprising a guide RNA that targets a selected DNA sequence and a Cas protein capable of modifying the selected DNA sequence; whereby a nucleic acid molecule encoding at least one of said guide RNA or Cas protein is operably connected in the cell with a regulatory element comprising a promoter of said gene of interest, and whereby expression of at least one CRISPR-Cas system component is driven by the promoter of the gene of interest; and determining expression of said gene of interest based on detection of the modification of said selected DNA sequence.

In a related aspect, the invention provides in recombinant cells which are obtained or obtainable by the methods as described herein. In particular, in an aspect, the invention relates to a recombinant cell comprising, introduced into said cell, one or more nucleic acid molecules encoding a CRISPR-Cas system comprising a guide RNA that targets a selected recorder DNA sequence and a Cas protein capable of modifying a targeted locus, whereby at least one of said nucleic acid molecules encoding at least one of said guide RNA or Cas protein is operably connected with a regulatory element comprising a promoter that is activated in parallel to a cellular event or as a consequence of the cellular event, in particular, an endogenous gene of interest. The invention also relates to the use of such recombinant cell for any of the methods according to the invention as described herein. In particular, in an aspect, the invention relates to the use of a recombinant cell according to the invention as described herein for encoding, capturing, or recording cellular events or cellular history or for determining expression of a gene of interest.

In yet another aspect, the invention relates to an organism, such as a non-human organism, comprising one or more of a recombinant cell (population) according to the invention as described herein.

In further aspects, the invention relates to kits comprising one or more, or all of the components of the CRISPR/Cas system for performing the methods of the invention as described herein. In alternative aspects, the invention relates to kits comprising one or more of a recombinant cell (population) according to the invention as described herein.

In certain embodiments, the present invention provides for two or more guide RNAs in a redundant encoding methodology. In an embodiment, the invention provides for at least one guide RNA in a redundant encoding methodology. The at least one guide RNA may be operably connected to a regulatory element comprising a promoter that is activated in parallel to a cellular event or as a consequence to a cellular event. The guide RNA may target multiple recorder DNA sequences. The two or more guide RNAs may be operably connected with a regulatory element comprising a promoter that is activated in parallel to a cellular event or as a consequence of a cellular event. In other words, at least two guide RNAs are expressed in parallel to a cellular event or as a consequence of a cellular event. Each guide RNA may be specific or targeted to a different recorder DNA sequence, whereby upon the cellular event at least one recorder DNA sequence will be modified. Not being bound by a theory, the use of redundant targeting by CRISPR increases the sensitivity of cellular recording, such that at least one recorder DNA sequence will be detectably modified, thus allowing the cellular activity to be recorded.

In certain embodiments, the regulatory element comprising a promoter according to the present invention includes a promoter that is an RNA polymerase II (pol II) promoter. Not being bound by a theory, the use of transcription factors responsive to cellular activities may require Pol II promoters. The guide RNA may be flanked by two ribozymes to allow expression from Pol II promoters. Other strategies may include RNA-triple-helix structures, introns, microRNAs, and ribozymes, with Cas9-based CRISPR-TFs and Cas6/Csy4-based RNA processing. Not being bound by a theory flanking ribozyme sequences allow self-catalyzed cleavage to generate the desired gRNA.

In another aspect, the present invention provides for a method of recording a cellular event in a cell and detecting the occurrence of the cellular event at a point of assay after the event has occurred comprising: (a) providing a cell comprising a recombinase operably connected in the cell with a regulatory element comprising a promoter that is activated in parallel to the cellular event or as a consequence of the cellular event, and a recorder DNA sequence comprising recombination sites for said recombinase, whereby expression of the recombinase is driven by the promoter; and (b) detecting the occurrence of the cellular event based on detection of the recombination of said recorder DNA sequence. The recorder DNA sequence may comprise a reversed promoter and recombination of the reversed promoter may activate expression of a detectable reporter molecule. The detectable reporter molecule may be an altered sequence as a result of recombination or could be a surface, luminescent, or fluorescent marker.

In another aspect, the present invention provides for a recombinant cell comprising a nucleic acid molecule encoding a recombinase operably connected with a regulatory element comprising a promoter that is activated in parallel to a cellular event or as a consequence of a cellular event and a recorder DNA sequence comprising recombination sites for said recombinase. In an embodiment, the invention provides for a recombinant cell comprising a nucleic acid molecule encoding a recombinase operably connected with a regulatory element comprising a promoter that is activated in parallel to a cellular event, wherein the cellular event is coupled to a single cell genomic readout.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is intended as a promise.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 9 illustrates that both DNA and RNA can be analyzed in a single cell, such that changes in recorder DNA sequences indicates that a cellular event has occurred in the cell, and changes in RNA expression can be attributed to cells where the cellular event occurred and in cells where the cellular event has not occurred.

FIG. 11 illustrates HEK293T cells transfected with a two plasmid system including a recombinase and recombination RFP reporter. A) Bxb1 recombinase, B) φC31 recombinase. The cells were first imaged in bright field and then imaged for RFP fluorescence.

DETAILED DESCRIPTION OF THE INVENTION

Figure 1:
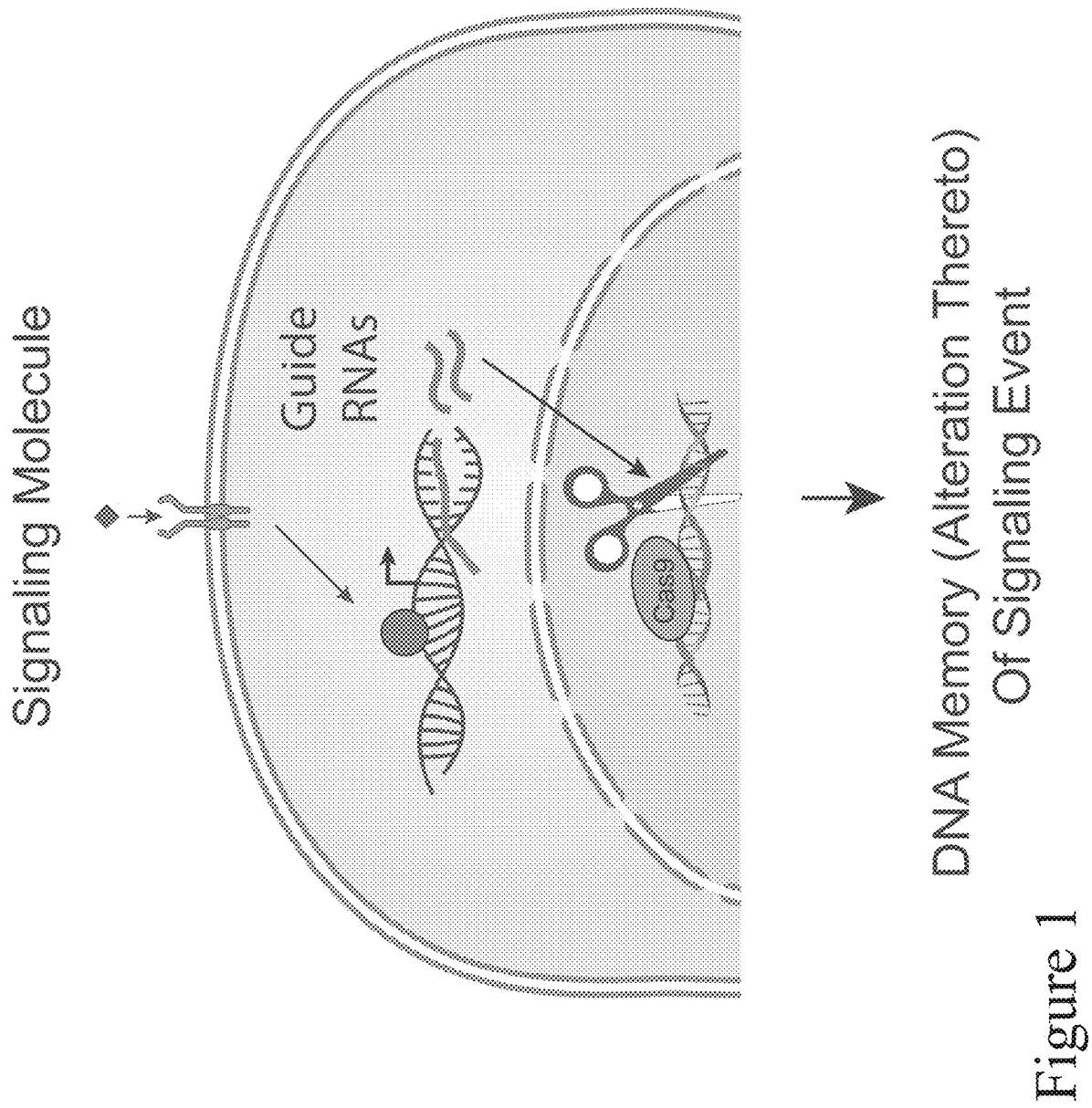
FIG. 1 illustrates a recording system where as a consequence of a signaling molecule binding to a receptor, transcription of a guide RNA targeting a recorder DNA sequence is initiated. The modified recorder DNA is a record of the signaling molecule binding.
Figure 2:
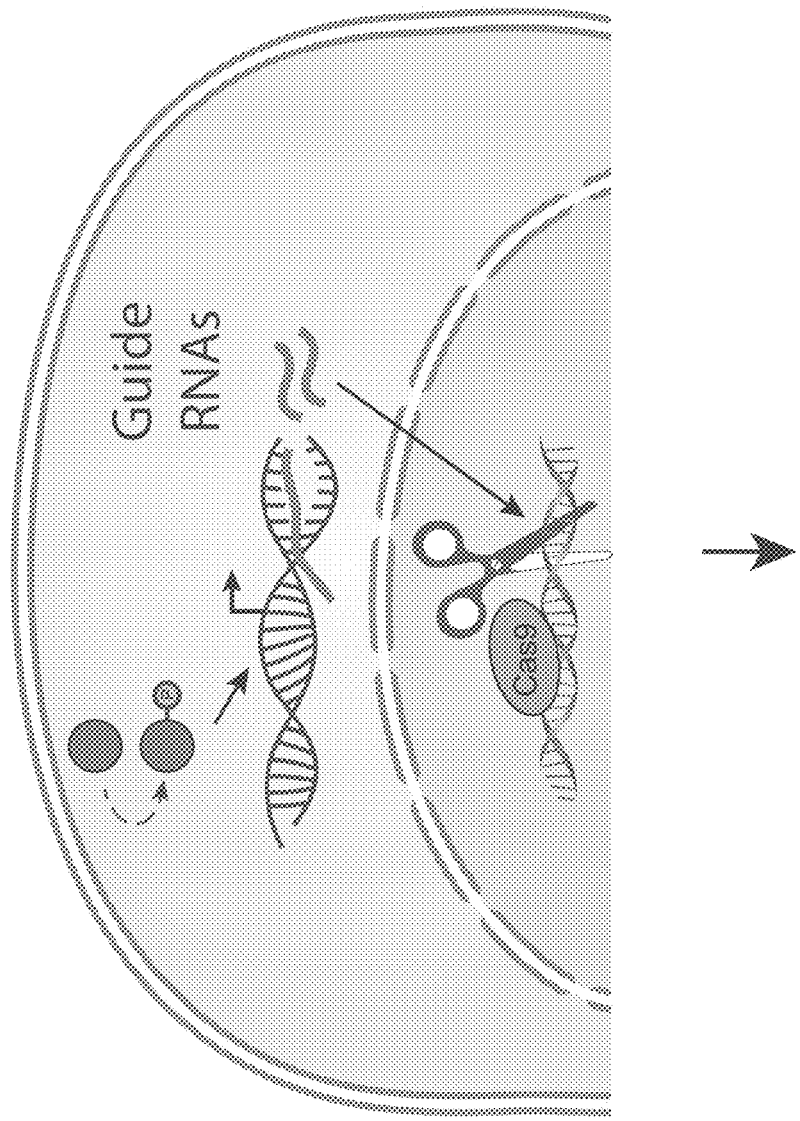
FIG. 2 illustrates phosphorylation of a transcription factor causes guide RNA expression and modification of the recorder DNA.
Figure 3:
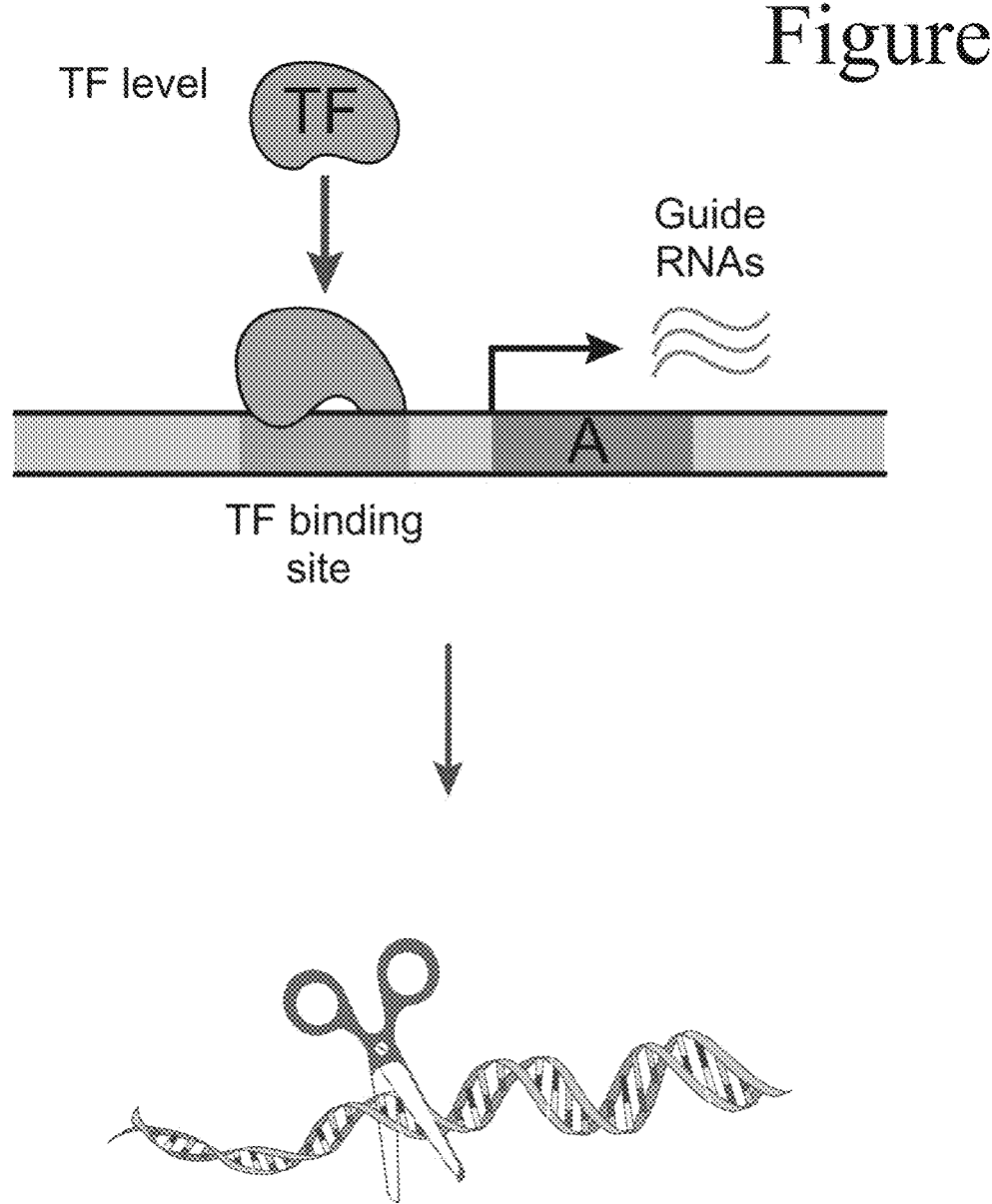
FIG. 3 illustrates transcription factor binding and guide RNA expression.
Figure 4:
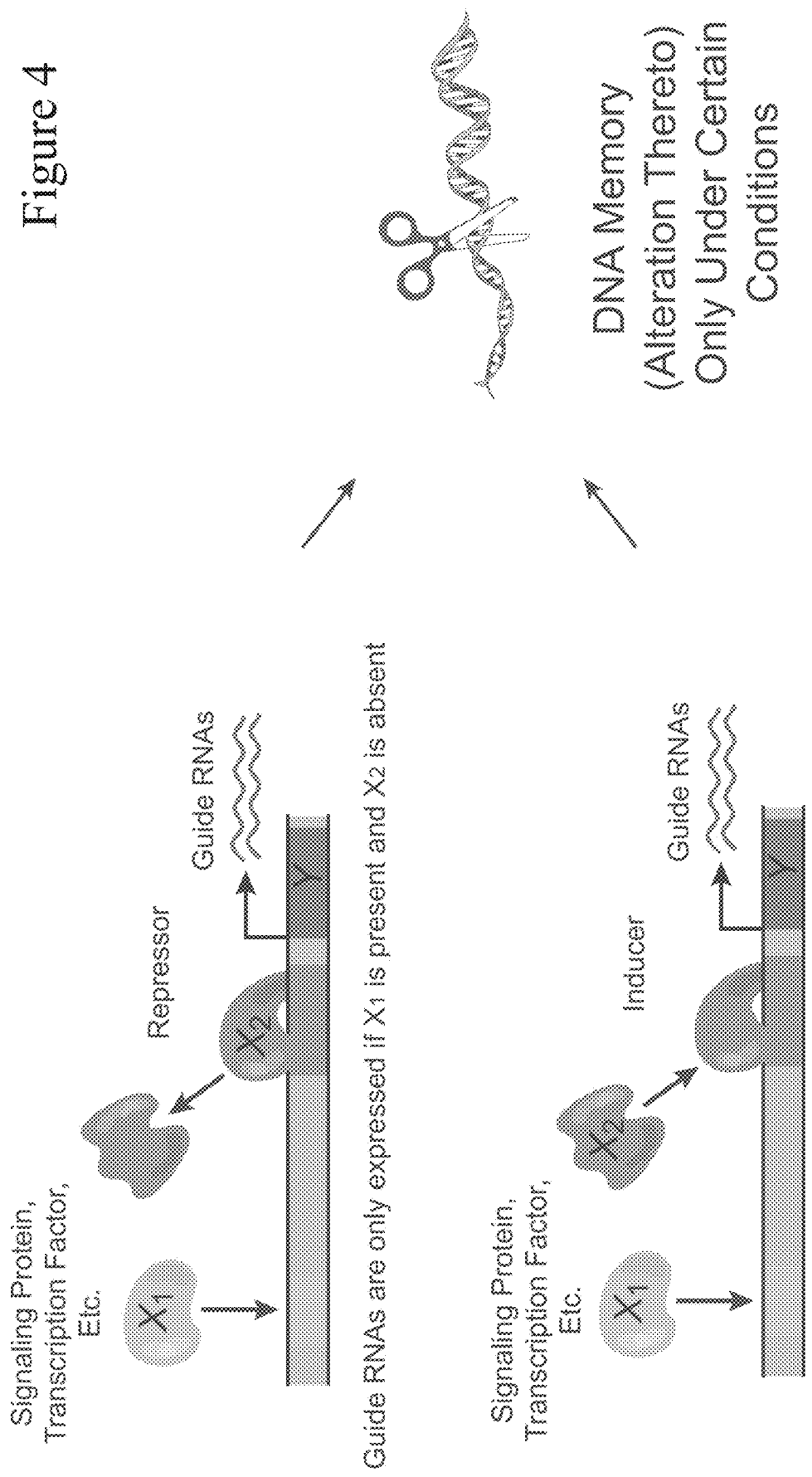
FIG. 4 illustrates expression of guide RNA only when certain conditions are met.
Figure 5:
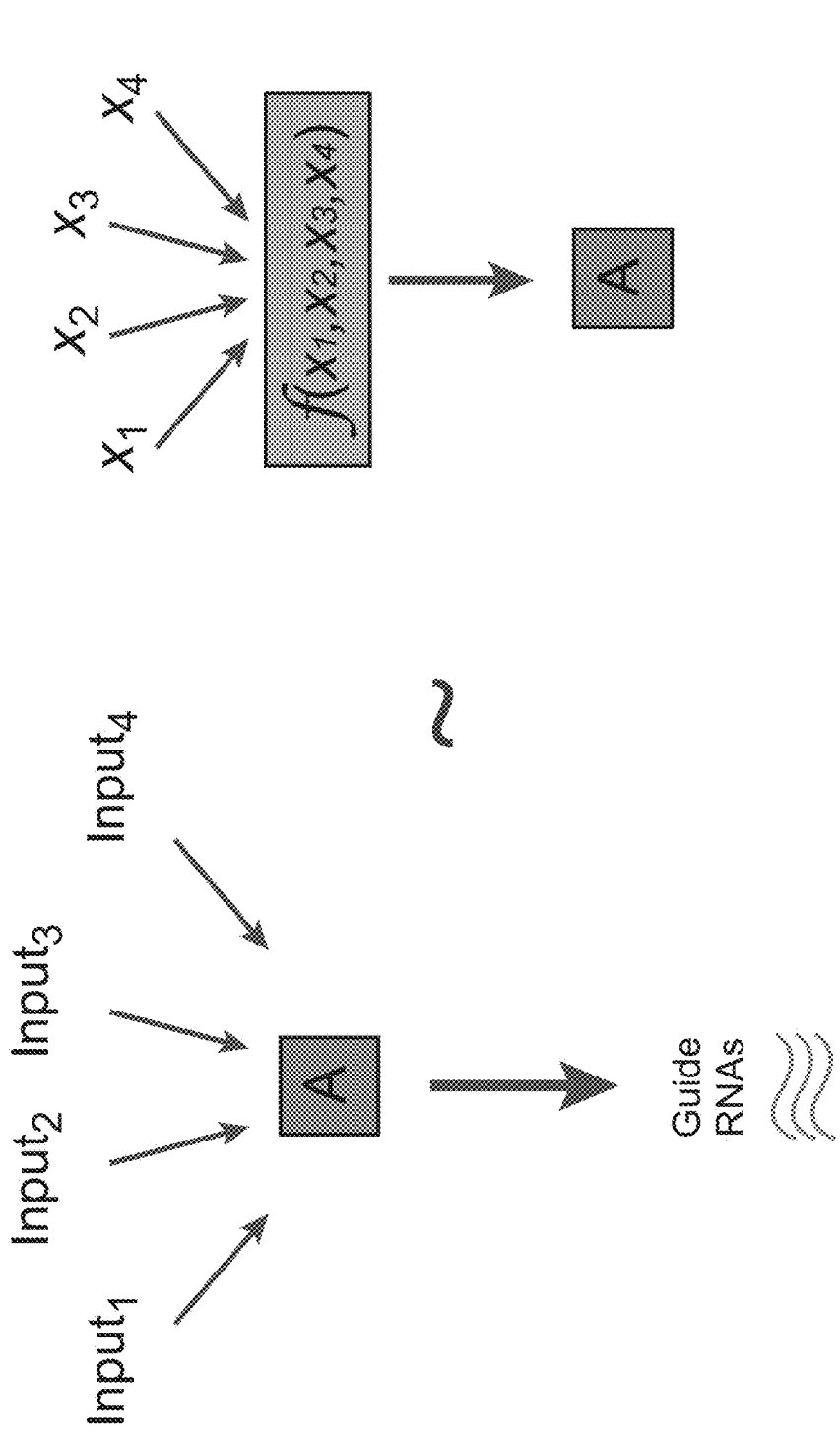
FIG. 5 illustrates that guide RNA expression can be dependent upon multiple factors or conditions.
Figure 6:
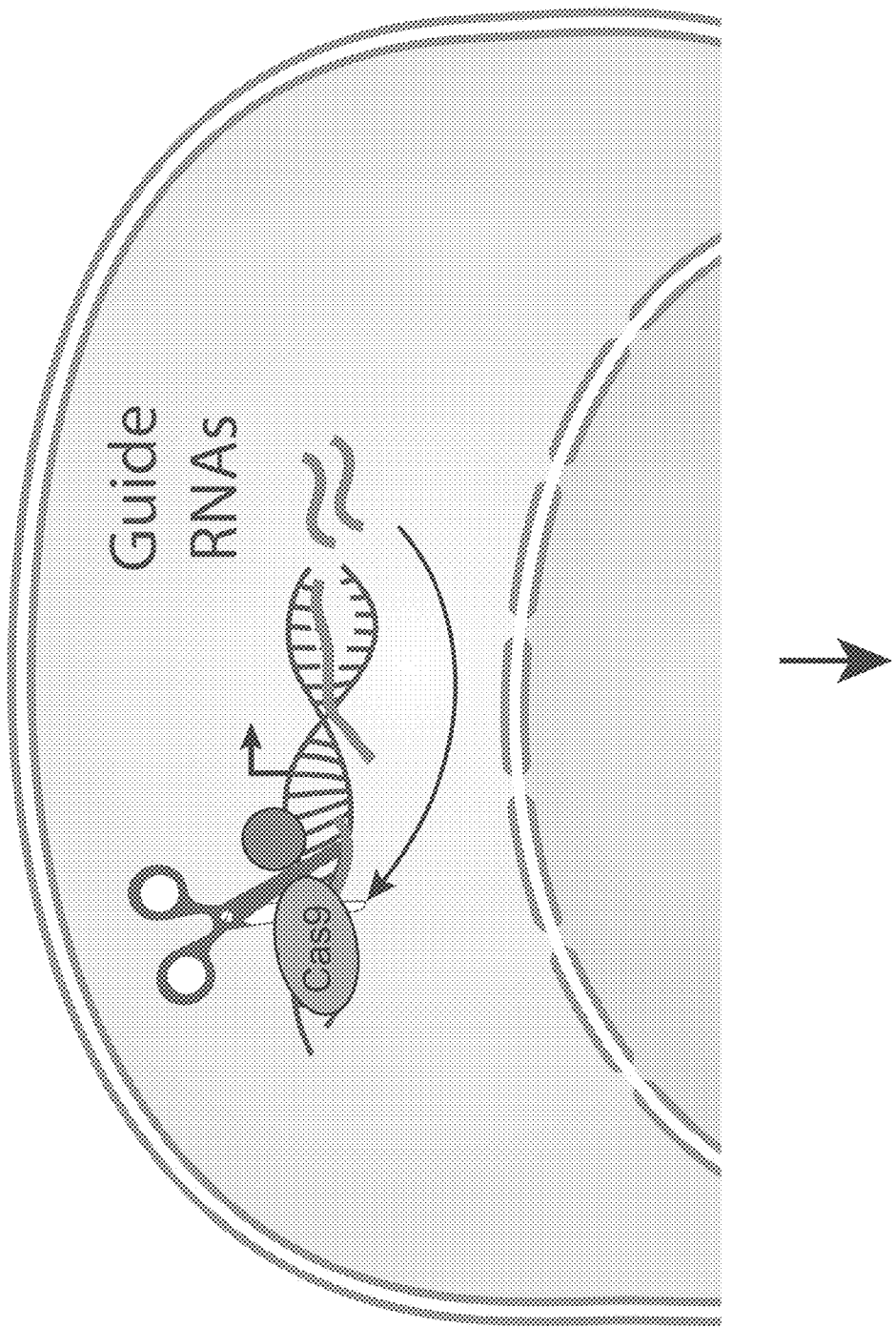
FIG. 6 illustrates feedback regulation of guide RNA expression.
Figure 7:
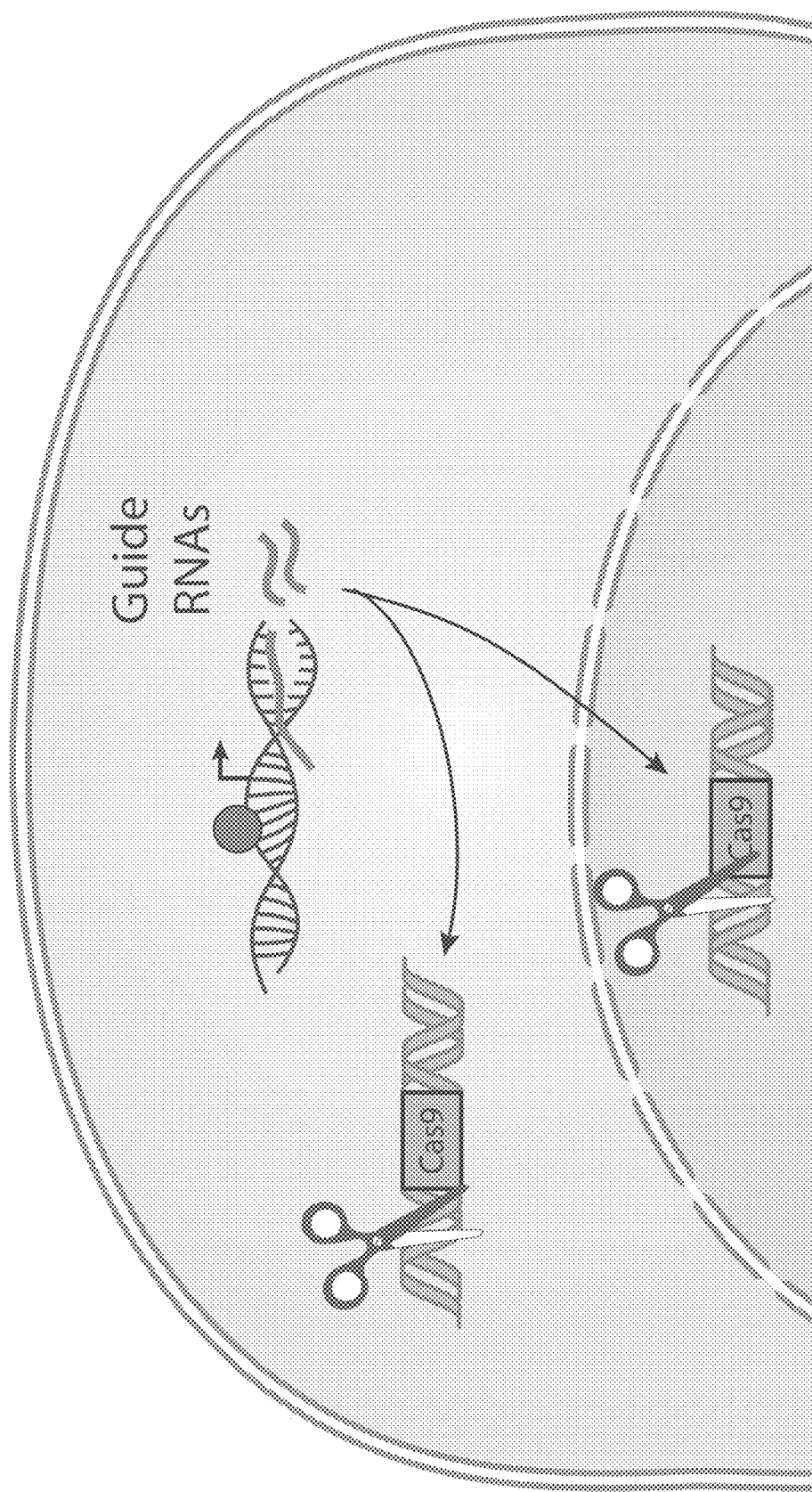
FIG. 7 illustrates self inactivation by expression of guide RNA targeting Cas9.
Figure 8:
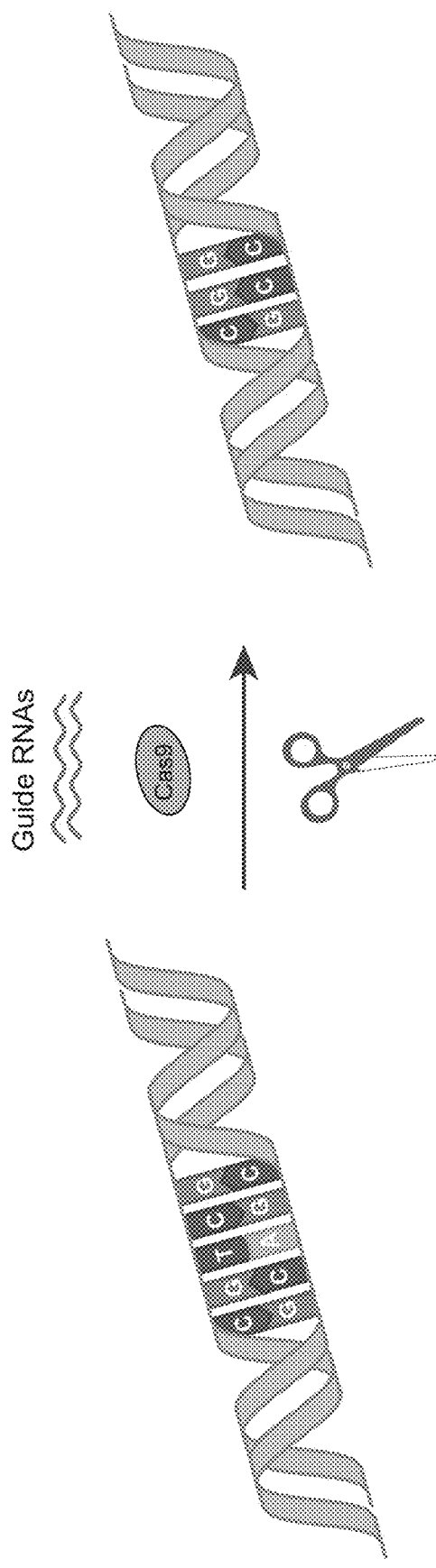
FIG. 8 illustrates that the recorder DNA can be modified such that the cellular event can be determined by DNA sequencing.

Before the present methods of the invention are described, it is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

As used herein, the singular forms "a" "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of". It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. It may be advantageous in the practice of the invention to be in compliance with Art. 53(c) EPC and Rule 28(b) and (c) EPC. Nothing herein is intended as a promise.

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); the series Methods in Enzymology (Academic Press, Inc.); Innis et al., PCR Protocols: A Guide to Methods and Applications, Academic Press: San Diego, 1990; PCR 2: A Practical Approach (M. J. MacPherson, B. D. Hames and G. R. Taylor eds. (1995); Harlow and Lane, eds. (1988) Antibodies, a Laboratory Manual; and Animal Cell Culture (R. I. Freshney, ed. (1987). General principles of microbiology are set forth, for example, in Davis, B. D. et al., Microbiology, 3rd edition, Harper & Row, publishers, Philadelphia, Pa. (1980).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the following detailed description of the invention, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

It is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

Preferred statements (features) and embodiments of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below numbered statements and embodiments 1 to 76, with any other statement and/or embodiments.

1. A method of determining expression of a gene of interest in a cell comprising providing a cell comprising a CRISPR-Cas system, said CRISPR-Cas system comprising a guide RNA that targets a selected DNA sequence and a Cas protein capable of modifying the selected DNA sequence; whereby a nucleic acid molecule encoding at least one of said guide RNA or Cas protein is operably connected in the cell with a regulatory element comprising a promoter of said gene of interest, and whereby expression of at least one CRISPR-Cas system component is driven by the promoter of the gene of interest; and determining expression of said gene of interest based on detection of the modification of said selected DNA sequence.

2. The method according to statement 1, wherein said method further comprises introducing in said cell a vector comprising said selected DNA sequence and said method comprises detection of the modification of said selected DNA sequence on said vector.

3. The method according to statement 1 or 2, wherein said selected DNA sequence is not endogenous to said cell.

4. The method according to statement 1 or 2, wherein said selected DNA sequence is a sequence endogenous to said cell and selected based on its minimal impact on the functioning of the cell after modification by the CRISPR-Cas system.

5. The method according to any of statements 1 to 4, wherein said selected DNA sequence is not comprised in said gene of interest.

6. The method according to any of statements 1 to 5, wherein said CRISPR-Cas system does not modify the expression of said gene of interest.

7. The method according to any of statements 1 to 6, wherein said CRISPR-Cas system is multiplexed.

8. The method according to any of statements 1 to 7, in which the cell encodes more than one guide RNA, whereby a first guide RNA targets a first selected DNA sequence for determining the expression of a first gene of interest and a second guide RNA targets a second selected DNA sequence different from said first selected DNA sequence for determining the expression of a second gene of interest.

9. The method according to statement 8, wherein said second selected DNA sequence targeted by the second guide RNA provided for determining the expression of said second gene of interest is present in the cell only after said modification by said Cas protein of said first selected DNA sequence provided for determining the expression of said first gene of interest.

10. The method according to statement 8, wherein said second selected DNA sequence targeted by the second guide RNA provided for determining the expression of said second gene of interest is present in the cell only before said modification by said Cas protein of said first selected DNA sequence provided for determining the expression of said first gene of interest.

11. The method according to any of statements 1 to 10, wherein said modification of said selected DNA sequence comprises inducing one or more mutations in said selected DNA sequence.

12. The method according to any of statements 1 to 11, wherein said modification of said selected DNA sequence comprises the introduction, deletion, or substitution of one or more nucleotides in said selected DNA sequence.

13. The method of any of statements 1 to 12, wherein said modification comprises detection by DNA sequencing, PCR, hybridization, RFLP, AFLP.

14. The method of any of statements 1 to 13, wherein said modification comprises detection by single cell PCR.

15. The method of any of statements 1 to 14, wherein said modification comprises detection by single cell DNA or RNA sequencing.

16. The method according to any of statements 1 to 15 which comprises, introducing into said cell a nucleic acid molecule encoding:
(A) a CRISPR-Cas system comprising a Cas protein and one or more guide RNAs that target said selected DNA sequence, whereby the Cas protein modifies said selected DNA sequence; or
(B) either one of:
(a) one or more CRISPR-Cas system guide RNAs that hybridize with a selected DNA sequences, or
(b) a Cas protein.

17. The method according to any of statements 1 to 16, wherein said cell is a eukaryotic cell.

18. The method according to any of statements 1 to 17, wherein said guide RNA, said Cas protein, or both are conditionally and/or inducibly expressed in said cell.

19. The method according to any of statements 1 to 18, wherein said guide RNA comprises a guide sequence, a tracr mate sequence and a tracr sequence.

20. The method according to statement 19, wherein said guide sequence and said tracr mate sequence are arranged in a 5' to 3' orientation on a single nucleic acid molecule.

21. The method according to statement 19 or 20, wherein said guide sequence, said tracr mate sequence, and said tracr sequence are arranged in a 5' to 3' orientation on a single nucleic acid molecule.

22. The method according to any of statements 19 to 21, wherein when transcribed, the tracr mate sequence hybridizes to the tracr sequence and the guide sequence directs sequence-specific binding of a CRISPR complex to the target sequence, wherein the CRISPR complex comprises the Cas complexed with (1) the guide sequence that is hybridized to the target sequence, and (2) the tracr mate sequence that is hybridized to the tracr sequence.

23. The method according to any of statements 1 to 22, wherein said guide RNA comprises a single guide RNA.

24. The method according to any of statements 1 to 23, wherein the guide RNA; or the tracr, tracr mate, and guide sequence together, comprise two or more hairpins.

25. The method according to any of statements 1 to 24, wherein said guide RNA, said Cas protein, or both are introducing into the cell by a delivery system comprising viral particles, liposomes, electroporation, microinjection or conjugation.

26. The method according to any of statements 1 to 25, wherein said guide RNA, said Cas protein, or both are introduced in said cell by means of transduction.

27. The method according to any of statements 1 to 26, wherein said guide, said Cas protein, or both are introduced in said cell by means of lentiviral, retroviral, adenoviral, or AAV transduction.

28. The method according to any of statements 1 to 27, wherein the Cas protein is codon optimized for expression in a eukaryotic cell.

29. The method according to any of statements 1 to 28, wherein said Cas is a type II Cas.

30. The method according to any of statements 1 to 29, wherein said Cas is Cas9.

31. The method according to any of statements 1 to 30, wherein said Cas is a Cas originating from *Streptococcus pyogenes, Streptococcus thermophiles*, or *Staphylococcus aureus*.

32. The method according to any of statements 1 to 31, wherein said Cas is a mutated Cas having an altered catalytic activity.

33. The method according to any of statements 1 to 32, wherein said Cas is a mutated Cas having a nickase activity.

34. The method according to any of statements 1 to 33, wherein said Cas comprises at least one or more nuclear localization sequences (NLSs).

35. The method according to any of statements 1 to 34, wherein said Cas comprises at least one or more nuclear localization sequences (NLSs) in the proximity of a terminus of the CRISPR enzyme.

36. The method according to any of statements 1 to 35, wherein the method is conducted in vivo in a non-human organism or ex vivo on a cell taken from said organism, optionally wherein said cell is returned to said organism.

37. A recombinant cell comprising, introduced into said cell, one or more nucleic acid molecules encoding a CRISPR-Cas system comprising a guide RNA that targets a selected DNA sequence and a Cas protein capable of modifying a targeted genomic locus, whereby at least one of said nucleic acid molecules encoding at least one of said guide RNA or Cas protein is operably connected with a regulatory element comprising a promoter of a gene of interest.

38. The recombinant cell according to statement 37, wherein said selected DNA sequence is not endogenous to said cell.

39. The recombinant cell according to statement 37 or 38, wherein said selected DNA sequence is a sequence endogenous to said cell and selected based on its minimal impact on the functioning of the cell after modification by the CRISPR-Cas system.

40. The recombinant cell according to statement 37 or 38, whereby said selected DNA sequence is not comprised in said gene of interest.

41. The recombinant cell according to any of statements 37 to 40, wherein said CRISPR-Cas system does not modify the expression of said gene of interest.

42. The recombinant cell according to any of statements 37 to 41, wherein said cell comprises, operably connected with a regulatory element comprising a promoter of a gene of interest, a nucleic acid molecule encoding either:
(A) a CRISPR-Cas system comprising a Cas protein and one or more guide RNAs that target said selected DNA sequence, whereby the Cas protein modifies said selected DNA sequence; or
(B) either one of:
(a) one or more CRISPR-Cas system guide RNAs that hybridize with a selected DNA sequences,
or
(b) a Cas protein; wherein said cell further comprises a guide RNA that targets said selected DNA sequence.

43. The recombinant cell according to any of statements 37 to 42, wherein said cell is a eukaryotic cell.

44. The recombinant cell according to any of statements 37 to 43, wherein said guide RNA, said Cas protein, or both are capable of being conditionally and/or inducibly expressed in said cell.

45. The recombinant cell according to any of statements 37 to 44, wherein said guide RNA comprises a guide sequence, a tracr mate sequence and a tracr sequence.

46. The recombinant cell according to statement 45, wherein said guide sequence and said tracr mate sequence are arranged in a 5' to 3' orientation on a single nucleic acid molecule.

47. The recombinant cell according to statement 45 or 46, wherein said guide sequence, said tracr mate sequence, and said tracr sequence are arranged in a 5' to 3' orientation on a single nucleic acid molecule.

48. The recombinant cell according to any of statements 45 to 47, wherein when transcribed, the tracr mate sequence hybridizes to the tracr sequence and the guide sequence directs sequence-specific binding of a CRISPR complex to the target sequence,
wherein the CRISPR complex comprises the Cas complexed with (1) the guide sequence that is hybridized to the target sequence, and (2) the tracr mate sequence that is hybridized to the tracr sequence.

49. The recombinant cell according to any of statements 37 to 48, wherein said guide RNA comprises a single guide RNA.

50. The recombinant cell according to any of statements 37 to 49, wherein the guide RNA; or the tracr, tracr mate, and guide sequence together, comprise two or more hairpins.

51. The recombinant cell according to any of statements 37 to 50, wherein a nucleic acid encoding said guide RNA, said Cas protein, or both is genomically integrated in said cell.

52. The recombinant cell according to any of statements 37 to 51, wherein a nucleic acid encoding said guide RNA, said Cas protein, or both is extra-chromosomal in said cell.

53. The recombinant cell according to any of statements 37 to 52, wherein the Cas protein is codon optimized for expression in a eukaryotic cell.

54. The recombinant cell according to any of statements 37 to 53, wherein said Cas is a type II Cas.

55. The recombinant cell according to any of statements 37 to 54, wherein said Cas is Cas9.

56. The recombinant cell according to any of statements 37 to 55, wherein said Cas is a Cas originating from *Streptococcus pyogenes, Streptococcus thermophiles*, or *Staphylococcus aureus*.

57. The recombinant cell according to any of statements 37 to 56, wherein said Cas is a mutated Cas having an altered catalytic activity.

58. The recombinant cell according to any of statements 37 to 57, wherein said Cas is a mutated Cas having a nickase activity.

59. The recombinant cell according to any of statements 37 to 58, wherein said Cas comprises at least one or more nuclear localization sequences (NLSs).

60. The recombinant cell according to any of statements 37 to 59, wherein said Cas comprises at least one or more nuclear localization sequences (NLSs) in the proximity of a terminus of the CRISPR enzyme.

61. A kit comprising the recombinant cell according to any of statements 37 to 60.

62. The kit according to statement 61, further comprising instructions for performing the method according to any of statements 1 to 36.

63. A non-human organism comprising the recombinant cell according to any of statements 37 to 60.

64. The non-human organism according to statement 63, wherein said organism is a eukaryotic organism.

65. The non-human organism according to statement 63 or 64, wherein said organism is a plant or animal organism.

66. The non-human organism according to any of statements 63 to 65, wherein said organism is a mammal.

67. A method for analyzing cellular events or cellular history, comprising determining expression of a gene of interest in a cell according to any of statements 1 to 36.

68. A method for encoding or recording cellular events or cellular history in a cell comprising
providing a cell comprising a CRISPR-Cas system, said CRISPR-Cas system comprising a guide RNA that targets a selected DNA sequence and a Cas protein capable of modifying the selected DNA sequence; whereby a nucleic acid molecule encoding at least one of said guide RNA or Cas protein is operably connected in the cell with a regulatory element comprising a promoter of a gene of interest, and whereby expression of at least one CRISPR-Cas system component is driven by the promoter of the gene of interest; thereby recording cellular events or cellular history as modification of said selected DNA sequence.

69 A method of recording a cellular event in a cell and detecting the occurrence of the cellular event at a point of assay after the event has occurred comprising:
(a) providing a cell comprising a CRISPR-Cas system, said CRISPR-Cas system comprising at least one guide RNA that targets a selected recorder DNA sequence and a Cas protein capable of modifying the selected recorder DNA sequence; whereby a nucleic acid molecule encoding at least one of said guide RNA or Cas protein is operably connected in the cell with a regulatory element comprising a promoter that is activated in parallel to the cellular event or as a consequence of the cellular event, and whereby expression of at least one CRISPR-Cas system component is driven by the promoter; and (b) detecting the occurrence of the cellular event based on detection of the modification of said selected recorder DNA sequence.

70. The method according to statement 69, wherein the cellular event is a change in expression of a gene of interest, a change in level of a protein of interest, a change in the level of an intracellular molecule, a change in a posttranslational modification, a change in the activity of a molecule of interest, a change in microenvironment, exposure to a factor of interest, activation of a transcription factor, deactivation of a transcriptional repressor, recruitment of a transcription factor, activation of a signal transduction pathway, or remodeling of chromatin.

71. The method according to statements 69 or 70, wherein the promoter is a promoter of a gene of interest.

72. The method according to any of statements 69 to 71, wherein the promoter is responsive to a specific transcription factor.

73. The method according to statement 72, wherein the transcription factor is recruited to the promoter as a result of activation of a signal transduction pathway.

74. The method of statement 72 or 73, wherein the promoter is responsive to a nuclear receptor.

75. The method of statement 70, wherein exposure to a factor of interest comprises exposure to a chemical, signaling molecule, or pathogen.

76. The method according to any of statements 69 to 75, wherein the promoter is responsive to an exogenous agent.

In an aspect, the invention relates to a method of determining expression of a gene of interest in a cell comprising expressing in said cell a CRISPR-Cas system comprising a guide RNA that targets a selected DNA sequence and a Cas protein capable of modifying the selected DNA sequence; whereby a nucleic acid molecule encoding at least one of said guide RNA or Cas protein is operably connected in the cell with a regulatory element comprising a promoter of said gene of interest, and whereby expression of at least one CRISPR-Cas system component is driven by the promoter of the gene of interest; and determining expression of said gene of interest based on detection of the modification of said selected DNA sequence.

In a related aspect, the invention relates to a method for encoding or recording cellular events or cellular history in a cell comprising expressing in said cell a CRISPR-Cas system comprising a guide RNA that targets a selected DNA sequence and a Cas protein capable of modifying the selected DNA sequence; whereby a nucleic acid molecule encoding at least one of said guide RNA or Cas protein is operably connected in the cell with a regulatory element comprising a promoter of a gene of interest, and whereby expression of at least one CRISPR-Cas system component is driven by the promoter of the gene of interest; thereby recording cellular events or cellular history as modification of said selected DNA sequence.

In a further related aspect, the invention relates to a method for analyzing cellular events or cellular history, comprising determining expression of a gene of interest in a cell comprising expressing in said cell a CRISPR-Cas system comprising a guide RNA that targets a selected DNA sequence and a Cas protein capable of modifying the selected DNA sequence; whereby a nucleic acid molecule encoding at least one of said guide RNA or Cas protein is operably connected in the cell with a regulatory element comprising a promoter of said gene of interest, and whereby expression of at least one CRISPR-Cas system component is driven by the promoter of the gene of interest; and determining expression of said gene of interest based on detection of the modification of said selected DNA sequence.

As used herein, the term "determining expression" is linked to the detection of a CRISPR/Cas mediated modification of a selected target DNA sequence. This term encompasses the determination of whether a gene of interest has been expressed in the past. Determining expression therefore relates to determining whether a gene of interest is or has been expressed. It will be understood that only if the CRISPR-Cas system is present in the cell the selected DNA sequence can be modified. Hence, determining past expression of a gene of interest is subject to the presence of the CRISPR-Cas system.

As used herein, the term "encoding or recording cellular events or cellular history" refers to permanently fixing the history of a cellular event as modification of selected target DNA sequences. The modification of selected target DNA sequences can be used as a readout of (past) cellular events. "cellular events" or "cellular history" in this context refers to history of a change in expression of a gene of interest, a change in level of a protein of interest, a change in the level of an intracellular molecule, a change in a posttranslational modification, a change in the activity of a factor of interest, a change in microenvironment, exposure to a molecule of interest, activation of a transcription factor, deactivation of a transcriptional repressor, recruitment of a transcription factor, activation of a signal transduction pathway, or remodeling of chromatin.

The gene of interest according to the present invention can be any type of gene, and is not limited by structure or function. By means of example and without limitation, the gene of interest may be a transcription factor, enzyme, ribosomal gene, structural gene, miRNA, etc. and may be involved in any type of cellular function, such as without limitation cell signaling, cell division, etc. It will be understood that preferably, the gene of interest is endogenous to the cell, i.e. a gene that originates from within said cell. Examples of genes of interest include genes associated with a signaling biochemical pathway, e.g., a signaling biochemical pathway-associated gene or polynucleotide. Examples genes of interest include a disease associated gene. A "disease-associated" gene refers to any gene which is yielding transcription or translation products at an abnormal level or in an abnormal form in cells derived from a disease-affected tissues compared with tissues or cells of a non disease control, such as oncogenes or tumor suppressor genes or metastasis suppressor genes. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The cell in which the CRISPR-Cas system is expressed according to the present invention can be any cell. In certain embodiments, the cell is a prokaryotic cell. In certain embodiments, the cell is a eukaryotic cell. Preferably, the cell is a eukaryotic cell, such as without limitation an animal or plant cell. In certain embodiments, the cell is a mammalian cell.

As used herein, the term "eukaryotic cell" may refer to a cell or a plurality of cells derived from a eukaryotic organism. In preferred embodiments, such eukaryotic cells are derived from an animal, such as mammal, primate, rodent, mouse, rat, rabbit, canine, dog, cow, bovine, sheep, ovine, goat, pig, fowl, poultry, chicken, fish, insect, or arthropod, preferably a mammal, such as a rodent, in particular a mouse. In certain embodiments, such eukaryotic cells are non-human eukaryotic cells. The cell type and cell origin are not particularly limiting according to embodiments of the invention. Eukaryotic cells may be primary cells or cell lines. Eukaryotic cells may be dividing cells (e.g. stem cells) or partially or terminally differentiated cells. Eukaryotic cells may in certain embodiments be tumor cells, which may or may not be capable of metastasis or which may or may not be derived from a metastatic tumor. Eukaryotic cells may also be in vitro transformed eukaryotic cells, e.g. in order to render them tumorigenic, whether or not with metastatic potential. Exemplary eukaryotic cell lines include, but are not limited to C8161, CCRF-CEM, MOLT, mIMCD-3, NHDF, HeLa-S3, Huh1, Huh4, Huh7, HUVEC, HASMC, HEKn, HEKa, MiaPaCell, Panel, PC-3, TF1, CTLL-2, C1R, Rat6, CV1, RPTE, A10, T24, 0.182, A375, ARH-77, Calu1, SW480, SW620, SKOV3, SK-UT, CaCo2, P388D1, SEMK2, WEHI-231, HB56, TIB55, Jurkat, J45.01 LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780eis, A172, A20, A253, A431, A-549, ALC, B16, B35, BCP-1 cells, BEAS-2B, bEnd.3, ! !-2 1. BR 293, BxPC3, C3H-10T1/2, C6/36, Cal-27, CHO, CHO-7, CeO-IR, CHO-K1, CHO-K2, CHQ-T, CHO Dhfr –/–, COR-L23, COR-L23/CPR, COR-L23/5010, CGR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, 562 cells, Ku812, KCL22, KG 1, KΛ'O1, LNCap, Ma-Mel 1-48, MC-38, MCF-7, MCF-IOA, MDA-MB-231, MDA-MB-468, MDA-MB-435, MDCK II, MOR/0.2R, MONO-MAC 6, MTD-1A, My End, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell expressing the CRISPR-Cas system as described herein is used to establish a new cell line comprising one or more vector-derived sequences. In some embodiments, a cell transiently transfected with the components of a CRISPR/Cas system as described herein (such as by transient transfection of one or more vectors, or transfection with RNA), and modified through the activity of a CRISPR complex, is used to establish a new cell line comprising cells containing the modification but lacking any other exogenous sequence.

As used herein, the term "non-human organism" or "non-human cell" refers to an organism or cell different than or not originating from *Homo sapiens*. As used herein, the term "non-human eukaryote" or "non-human eukaryotic cell" refers to a eukaryotic organism or cell different than or not derived from *Homo sapiens*. In preferred embodiments, such eukaryote (cell) is a non-human animal (cell), such as (a cell or cell population of a) non-human mammal, non-human primate, an ungulate, rodent (preferably a mouse or rat), rabbit, canine, dog, cow, bovine, sheep, ovine, goat, pig, fowl, poultry, chicken, fish, insect, or arthropod, preferably a mammal, such as a rodent, in particular a mouse. In some embodiments of the invention the organism or subject or cell may be (a cell or cell population derived from) an arthropod, for example, an insect, or a nematode. In some methods of the invention the organism or subject or cell is a plant (cell). In some methods of the invention the organism or subject or cell is (derived from) algae, including microalgae, or fungus. The skilled person will appreciate that the eukaryotic cells which may be transplanted or introduced in a non-human eukaryote according to the methods as referred to herein are preferably derived from or originate from the same species as the eukaryote to which they are transplanted. For example, a mouse cell is transplanted in a mouse in certain embodiment according to the methods of the invention as described herein. In certain embodiments, the eukaryote is an immunocompromized eukaryote, i.e. a eukaryote in which the immune system is partially or completely shut down. For instance, immunocompromized mice may be used in the methods according to the invention as described herein. Examples of immunocompromized mice include, but are not limited to Nude mice, RAG –/– mice, SCID (severe compromised immunodeficiency) mice, SCID-Beige mice, NOD (non-obese diabetic)-SCID mice, NOG or NSG mice, etc.

It will be understood that the CRISPR-Cas system as described herein is non-naturally occurring in said cell, i.e. engineered or exogenous to said cell. The CRISPR-Cas system as referred to herein has been introduced in said cell. Methods for introducing the CRISPR-Cas system in a cell are known in the art, and are further described herein elsewhere. The cell comprising the CRISPR-Cas system, or having the CRISPR-Cas system introduced, according to the invention comprises or is capable of expressing the individual components of the CRISPR-Cas system to establish a functional CRISPR complex, capable of modifying (such as cleaving) a target DNA sequence. Accordingly, as referred to herein, the cell comprising the CRISPR-Cas system can be a cell comprising the individual components of the CRISPR-Cas system to establish a functional CRISPR complex, capable of modifying (such as cleaving) a target DNA sequence. Alternatively, as referred to herein, and preferably, the cell comprising the CRISPR-Cas system can be a cell comprising one or more nucleic acid molecule encoding the individual components of the CRISPR-Cas system, which can be expressed in the cell to establish a functional CRISPR complex, capable of modifying (such as cleaving) a target DNA sequence.

According to the invention, a nucleotide sequence encoding at least one of said guide RNA or Cas protein is operably connected in the cell with a regulatory element comprising a promoter, whereby expression of at least one CRISPR-Cas system component is driven by the promoter. "operably connected" is intended to mean that the nucleotide sequence encoding the guide RNA and/or the Cas is linked to the regulatory element(s) in a manner that allows for expression of the nucleotide sequence, as also referred to herein elsewhere. The term "regulatory element" is also described herein elsewhere. According to the invention, the regulatory element comprises a promoter that is activated in parallel to a cellular event or as a consequence of the cellular event, such as preferably a promoter of an endogenous gene of interest. In certain embodiments, the promoter is at its endogenous genomic location. In such embodiments, the nucleic acid encoding the CRISPR and/or Cas is under transcriptional control of the promoter of the gene of interest at its native genomic location. In certain other embodiments, the promoter is provided on a (separate) nucleic acid molecule, such as a vector or plasmid, or other extrachromosomal nucleic acid, i.e. the promoter is not provided at its native genomic location. In certain embodiments, the promoter is genomically integrated at a non-native genomic location.

In certain embodiments, a nucleic acid encoding the guide RNA is operably connected in the cell with a regulatory element comprising a promoter of a gene of interest. In certain embodiments, a nucleic acid encoding the Cas is operably connected in the cell with a regulatory element comprising a promoter of a gene of interest. In certain embodiments a nucleic acid encoding the guide RNA is operably connected in the cell with a regulatory element comprising a promoter of a gene of interest and a nucleic acid encoding the Cas is operably connected in the cell with a regulatory element comprising a promoter of a gene of interest. In this latter case, the promoter driving the expression of the guide RNA and the Cas may be the same or may be different. In certain embodiments, a nucleic acid encoding the guide RNA and/or Cas is genomically integrated. In certain embodiments, a nucleic acid encoding the guide RNA and/or Cas is extrachromosomal or episomal. The nucleic acid encoding the guide RNA and the nucleic acid encoding the Cas may reside on the same or different nucleic acid molecules.

As used herein "selected DNA sequences" and "recorder DNA sequences" are used interchangeably. The selected recorder DNA sequences which are targeted by the guide RNA(s) according to the invention may be endogenous DNA sequences or exogenous DNA sequences. The selected DNA sequences which are targeted by the guide RNA(s), such as exogenous DNA sequences, according to the invention may be genomically integrated or may be extrachromosomal (e.g. provided on a plasmid or vector). In certain embodiments, the methods as described herein comprise introducing in the cell a vector or plasmid, by means known in the art as described herein elsewhere, said vector or plasmid comprising said selected DNA sequence and said method comprises detection of the modification of said selected DNA sequence on said vector. It will be understood that said vector or plasmid, or at least the selected DNA sequence comprised therein, may be genomically integrated, such as random integration or via homologous recombination. When the selected target DNA sequence is an endogenous sequence, it is preferred that the sequence is selected such that modification thereof has no or minimal impact on the (normal) functioning of the cell. The skilled person will readily identify such sequences by routine analysis or experimentation. In any case, it is preferred that such selected endogenous target DNA sequence does not reside in a coding sequence or ORF of a gene and/or does not reside in regulatory sequences of a gene (such as promoters, enhancers, silencers, etc.). Accordingly, the selected target DNA sequence is preferably selected to be phenotypically neutral after modification, or the cell before and after modification cannot be phenotypically distinguished from each other. Preferably, the selected target DNA sequence is selected such that gene expression before and after modification is unaltered. In a preferred embodiment, the selected target DNA sequence is not comprised in the gene of interest, such as is not comprised in the coding sequence or ORF of the gene of interest, or is not comprised in any of the regulatory sequences of the gene of interest. Accordingly, in certain embodiments, modification of the selected target DNA sequence does not alter the expression of the gene of interest. In other words, the CRISPR-Cas system in the methods according to the invention as described herein does not alter gene expression in the cell, such as does not alter gene expression of the gene of interest in the cell.

As described herein elsewhere, the selected target recorder DNA sequence is modified by the action of a functional CRISPR complex (i.e. the guide RNA complexed with the Cas protein, wherein the guide RNA comprises the guide sequence, tracr mate sequence and tracr sequence in 5' to 3' orientation, wherein the tracr sequence may or may not be on the same nucleic acid molecule as the guide sequence and tracr mate sequence). As used herein, "modified" essentially corresponds to mutated, i.e. the nucleic acid sequence of the target DNA sequence is altered, as described herein elsewhere, such as comprising point mutations, deletions, substitutions, or insertions of one or more nucleotides.

According to the invention, detection of the expression of a gene of interest (i.e. including expression at a previous point in time) is based on detection of the modification of the selected target recorder DNA sequence. Detecting the modification of the selected target sequence may be performed by any means suitable as known in the art. By means of example, and without limitation, detection may be carried out by methods involving sequencing, PCR, hybridization, RFLP, AFLP, etc. In certain embodiments, detection of the modifications of the selected DNA targets involve single cell detection, such as single cell PCR or sequencing (e.g. single cell DNA or RNA PCR or sequencing). Such techniques are known in the art. The skilled person will understand that if a certain gene of interest has not been expressed, no functional CRISPR complex has been formed, and hence the selected target DNA sequence has not been modified. The detection of the modification of the selected DNA target sequence allows discriminating between whether or not a gene of interest has been expressed. If the modification is detected, then the gene of interest has been expressed. If no modification is detected, then the gene of interest has not been expressed.

In certain embodiments, in the methods according to the invention as described herein the CRISPR-Cas system is multiplexed, i.e. multiple different guide RNAs can be provided. Each guide RNA may target (i.e. hybridize with) a different selected DNA target. Expression of the different guide RNAs may be driven by the different promoters based on the cellular event to be recorded. Accordingly, in certain embodiments, the methods of the invention as described herein are methods for determining more than one cellular event, such as at least two genes of interest in a cell comprising providing a cell comprising a CRISPR-Cas system, said CRISPR-Cas system comprising more than one, such as at least two guide RNAs that target a different selected DNA sequence and a Cas protein capable of modifying the selected DNA sequence; whereby each guide RNA is operably connected in the cell with a regulatory element comprising a promoter of a different gene of interest; and determining expression of said genes of interest based on detection of the modification of said respective selected DNA sequences. In certain embodiments, more than one different guide RNA may be operably connected in the cell with a regulatory element comprising a promoter of the same gene of interest. The different guide RNAs may be provided on different nucleic acid molecules or on the same nucleic acid molecule. The respective guide RNAs may be designed such that only modification of a first selected target DNA destroys a second selected target DNA. In this way, only if a first gene of interest is expressed, the modification of the selected target DNA sequence associated with the second gene of interest is present and can be modified, or vice versa only if a first gene of interest is not expressed, the modification of the selected target DNA sequence associated with the second gene of interest is present and can be modified. Such setup allows temporal recording of gene expression. Determination of the modification of the respective selected target DNA sequences allows to establish which gene of interest has been expressed first in time, i.e. which gene of interest has been expressed before another gene of interest.

In certain embodiments, one or more of the components of the CRISPR-Cas system may be conditionally (e.g tissue or cell type specific) and/or inducibly (e.g. chemically inducible) expressed in the cell. Inducible and conditional expression systems are described herein elsewhere. In particular embodiments, one or more of the guide RNA(s) may be conditionally and/or inducibly expressed in the cell. In particular preferred embodiments, the Cas may be conditionally and/or inducibly expressed in the cell.

As used herein, the term "targeting" of a selected DNA sequence means that a guide RNA is capable of hybridizing with a selected DNA sequence. As uses herein, "hybridization" or "hybridizing" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence.

As used herein, "expression" or "expressing" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic ceil. As used herein "expression" of a gene or nucleic acid encompasses not only cellular gene expression, but also the transcription and translation of nucleic acid(s) in cloning systems and in any other context.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or I, optical isomers, and amino acid analogs and peptidomimetics.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

In certain embodiments, the methods and cells according to the invention as described herein may be used in screening methods for therapeutic agents, and/or in diagnostic methods. Candidate therapeutic agents may have a different effect of temporal expression profiles, which may be read out according to the methods as described herein.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

As used herein, the terms "chimeric RNA", "chimeric guide RNA", "guide RNA", "single guide RNA" and "synthetic guide RNA" refer to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)". The guide sequence, tracr, and tracr mate sequence may be provided on a single nucleic acid molecule. Alternatively, the guide and tracr mate sequence may be provided on a single nucleic acid molecule, whereas the tracr is provided on a separate nucleic acid molecule.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213, 991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105, 035), US 2014-0186958 (U.S. application Ser. No. 14/105, 017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915, 150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836, 101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915, 260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGR-NAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096, 324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGET- ING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91(2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015).

Nishimasu et al., Crystal Structure of *Staphylococcus aureus* Cas9," Cell 162, 1113-1126 (Aug. 27, 2015).

Zetsche et al., "Cpf1 Is a Single RNA-Guided Endonuclease of a Class 2 CRISPR-Cas System," Cell 163, 1-13 (Oct. 22, 2015).

Shmakov et al., "Discovery and Functional Characterization of Diverse Class 2 CRISPR-Cas Systems," Molecular Cell 60, 1-13 (Available online Oct. 22, 2015).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.source-forge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence, i.e. an RNA capable of guiding Cas to a genomic target locus, may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNNXGG (SEQ ID NO: 1) where NNNNNNNNNNNNXGG (SEQ ID NO: 2) (N is A, G, T, or C; and X can be anything) has a single occurrence in the genome. A unique target sequence in a genome may include an S. pyogenes Cas9 target site of the form MMMMMMMMMNNNNNNNNNNNXGG (SEQ ID NO: 3) where NNNNNNNNNNNXGG (SEQ ID NO: 4) (N is A, G, T, or C; and X can be anything) has a single occurrence in the genome. For the S. thermophilus CRISPRI Cas9, a unique target sequence in a genome may include a Cas9 target site of the form MMMMMMMMNNNNNNNNNNNNXXAGAAW (SEQ ID NO: 5) where NNNNNNNNNNNNXXAGAAW (SEQ ID NO: 6) (N is A, G, T, or C; X can be anything; and W is A or T) has a single occurrence in the genome. A unique target sequence in a genome may include an S. thermophilus CRISPRI Cas9 target site of the form MMMMMMMMMNNNNNNNNNNNXXAGAAW (SEQ ID NO: 7) where NNNNNNNNNNNXXAGAAW (SEQ ID NO: 8) (N is A, G, T, or C; X can be anything; and W is A or T) has a single occurrence in the genome. For the S. pyogenes Cas9, a unique target sequence in a genome may include a Cas9 target site of the form MMMMMMMMNNNNNNNNNNNNXGGXG (SEQ ID NO: 9) where NNNNNNNNNNNNXGGXG (SEQ ID NO: 10) (N is A, G, T, or C; and X can be anything) has a single occurrence in the genome. A unique target sequence in a genome may include an S. pyogenes Cas9 target site of the form MMMMMMMMMNNNNNNNNNNNXGGXG (SEQ ID NO: 11) where NNNNNNNNNNNXGGXG (SEQ ID NO: 12) (N is A, G, T, or C; and X can be anything) has a single occurrence in the genome. In each of these sequences "M" may be A, G, T, or C, and need not be considered in identifying a sequence as unique. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNA fold, developed at Institute for Theoretical Chemistry at the University of Vienna, using the centroid structure prediction algorithm (see e.g. A. R. Gruber et al., 2008, Cell 106(1): 23-24; and P A Carr and G M Church, 2009, Nature Biotechnology 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactctcaagatt-taGAAAtaaatcttgcagaagctacaaagataaggctt catgccgaaat-caacaccctgtcatttatggcagggtgttttcgttatttaaTTTTTT (SEQ ID NO: 13); (2) NNNNNNNNNNNNNNNNNNNN-gttttgtactctcaGAAAtgcagaagctacaaagataaggctt-catgccgaaatca acaccctgtcatttatggcagggtgttttcgttatttaaT-TTTTT; (SEQ ID NO: 14) (3) NNNNNNN-NNNNNNNNNNNNNgttttgtactctcaGAAAtgcagaagcta-caaagataaggcttcatgccgaaatca acaccctgtcattt-tatggcagggtgtTTTTTT; (SEQ ID NO: 15) (4) NNNNNNNNNNNNNNNNNNNNgttt-tagagctaGAAAtagcaagttaaaataaggctagtccgttatcaacttgaaaa agtggcaccgagtcggtgcTTTTTT; (SEQ ID NO: 16) (5) NNNNNNNNNNNNNNNNNNNNgttt-tagagctaGAAATAGcaagttaaaataaggctagtccgttatcaacttgaa aaagtgTTTTTTT; and (SEQ ID NO: 17) (6) NNNNNNNNNNNNNNNNNNNNgttt-tagagctagAAATAGcaagttaaaataaggctagtccgttatcaTTTTT TTT (SEQ ID NO: 18). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

The RNAs to guide Cas, such as Cas9, can comprise CRISPR RNA and transactivating (tracr) RNA. The tracr mate and the tracr sequence can be connected to form a transactivating (tracer) sequence. The tracr mate and the tracr sequence can optionally be designed to form a single guide RNA (sgRNA). Indeed, it is advantageous that the RNAs to guide Cas can comprise chimeric single guide RNA (sgRNA). The tracr sequence and tracr mate sequence along the length of the shorter of the two when optimally aligned can be about or more than about 25%, 30%, 40%, 50%, 60%, 70%, 80%, 90%, 95%, 97.5%, 99%, or higher. The tracr sequence can be about or more than about 5, 6, 7, 8, 9, 10, 11, 12, 13, 14, 15, 16, 17, 18, 19, 20, 25, 30, 40, 50, or more nucleotides in length. The degree of complementarity between a guide sequence and its corresponding target sequence can be about or more than about 50%, 60%, 75%, 80%, 85%, 90%, 95%, 97.5%, 99%, or 100%. A guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. A guide or RNA or sgRNA can be less than about 75, 50, 45, 40, 35, 30, 25, 20, 15, 12, or fewer nucleotides in length.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example S. pyogenes Cas9 with the D10A mutation) can be delivered with a pair of guide RNAs targeting a site of interest. Guide sequences and strategies to minimize toxicity and off-target effects can be as in WO 2014/093622 (PCT/US2013/074667).

In some embodiments, the CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. A preferred Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, SpCas9 or SaCas9. It will be appreciated that SpCas9 or SaCas9 are those from or derived from *S. pyogenes* or *S. aureus* Cas9. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. The Cas enzyme can be for instance any naturally-occurring bacterial Cas9 as well as any chimaeras, mutants, homologs or orthologs. Many of the residue numberings used herein refer to the Cas9 enzyme from the type II CRISPR locus in *Streptococcus pyogenes* (annotated alternatively as SpCas9 or spCas9). However, it will be appreciated that this invention includes many more Cas9s from other species of microbes, e.g., orthologs of SpCas9, or Cas9s derived from microbes in addition to *S. pyogenes*, e.g., SaCas9 derived from *S. aureus*, St1Cas9 derived from *S. thermophilus* and so forth. The skilled person will be able to determine appropriate corresponding residues in Cas9 enzymes other than SpCas9 by comparison of the relevant amino acid sequences. Thus, where a specific amino acid replacement is referred to using the SpCas9 numbering, then, unless the context makes it apparent this is not intended to refer to other Cas9 enzymes, the disclosure is intended to encompass corresponding modifications in other Cas9 enzymes.

In some embodiments, the unmodified Cas has DNA cleavage activity, such as Cas9. In some embodiments, the Cas directs cleavage of one or both strands at the location of a target sequence, such as within the target sequence and/or within the complement of the target sequence. In some embodiments, the Cas directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a Cas that is mutated to with respect to a corresponding wild-type enzyme such that the mutated Cas lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a Cas is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Thus, the Cas may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A and/or one or more mutations in a RuvC1 or HNH domain of the Cas or has a mutation as otherwise as discussed herein. In one aspect of the invention, the Cas enzyme may be fused to a protein, e.g., a TAG, and/or an inducible/controllable domain such as a chemically inducible/controllable domain. The Cas in the invention may be a chimeric Cas proteins; e.g., a Cas having enhanced function by being a chimera. Chimeric Cas proteins may be new Cas containing fragments from more than one naturally occurring Cas. These may comprise fusions of N-terminal fragment(s) of one Cas9 homolog with C-terminal fragment(s) of another Cas homolog. The Cas can be delivered into the cell in the form of mRNA. The expression of Cas can be under the control of an inducible promoter.

Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, SpCas9 (*S. pyogenes* Cas9) or SaCas9 (*S. aureus* Cas9). StCas9" refers to wild type Cas9 from *S. thermophilus*, the protein sequence of which is given in the SwissProt database under accession number G3ECR1. Similarly, *S. pyogenes* Cas9 or SpCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCas9, St1Cas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. Without wishing to be bound by theory, it is believed that the target sequence should be associated with a PAM (protospacer adjacent motif); that is, a short sequence recognized by the CRISPR complex. The precise sequence and length requirements for the PAM differ depending on the Cas used, but PAMs are typically 2-5 base pair sequences adjacent the protospacer (that is, the target sequence. In some embodiments, the method comprises allowing a CRISPR complex to bind to the target polynucleotide to effect cleavage of said target polynucleotide thereby modifying the target polynucleotide, wherein the CRISPR complex comprises a Cas complexed with a guide sequence hybridized to a target sequence within said target polynucleotide, wherein said guide sequence is linked to a tracr mate sequence which in turn hybridizes to a tracr sequence. More aspects of the CRISPR system are described in Karginov and Hannon, The CRISPR system: small RNA-guided defence in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas to the DNA target consisting of the protospacer and the corresponding PAM via heteroduplex formation between the spacer region of the crRNA and the protospacer DNA. Finally, Cas mediates cleavage of target DNA upstream of PAM to create a DSB within the protospacer. A pre-crRNA array consisting of a single spacer flanked by two direct repeats (DRs) is also encompassed by the term "tracr-mate sequences"). In certain embodiments, Cas may be constitutively present or inducibly present or conditionally present or administered or delivered. Cas optimization may be used to enhance function or to develop new functions, one can generate chimeric Cas proteins. And Cas may be used as a generic DNA binding protein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

In some embodiments, the Cas as referred to herein is a codon optimized Cas. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way how the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus, such as for instance one or more oncogenic mutations, as for instance and without limitation described in Platt et al. (2014), Chen et al., (2014) or Kumar et al. (2009).

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV(SEQ ID NO: 19); the NLS from nucleoplasmin (e.g. the nucleoplasmin bipartite NLS with the sequence KRPAATKKAGQAKKKK) (SEQ ID NO: 20); the c-myc NLS having the amino acid sequence PAAKRVKLD (SEQ ID NO: 21) or RQRRNELKRSP (SEQ ID NO: 22); the hRNPA1 M9 NLS having the sequence NQSSNFGPMKGGNFGGRSSGPYGGGGQYFAK-PRNQGGY (SEQ ID NO: 23); the sequence RMRIZFKNKGKDTAELRRRRVEVSVELRKAKKD-EQILKRRNV (SEQ ID NO: 24) of the IBB domain from importin-alpha; the sequences VSRKRPRP (SEQ ID NO: 25) and PPKKARED (SEQ ID NO: 26) of the myoma T protein; the sequence PQPKKKPL (SEQ ID NO: 27) of human p53; the sequence SALIKKKKMAP (SEQ ID NO: 28) of mouse c-abl IV; the sequences DRLRR (SEQ ID NO: 29) and PKQKKRK (SEQ ID NO: 30) of the influenza virus NS1; the sequence RKLKKKIKKL (SEQ ID NO: 31) of the Hepatitis virus delta antigen; the sequence REKKKFLKRR (SEQ ID NO: 32) of the mouse Mx1 protein; the sequence KRKGDEVDGVDEVAKKKSKK (SEQ ID NO: 33) of the human poly(ADP-ribose) polymerase; and the sequence RKCLQAGMNLEARKTKK (SEQ ID NO: 34) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNAs) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, nature.com/mt/journal/v16/n9/abs/mt2008144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters-especially as to the numbers of RNAs or guides or sgRNAs discussed herein, without any undue experimentation.

The guide RNA(s), e.g., sgRNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the j-actin promoter, the phosphoglycerol kinase (PGK) promoter, and the EF1α promoter. An advantageous promoter is the promoter is U6.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR (i.e. guide RNA(s)) and/or Cas transcripts (e.g. nucleic acid transcripts, proteins, or enzymes) in prokaryotic or eukaryotic cells. For example, CRISPR and/or Cas transcripts can be expressed in bacterial cells such as Escherichia coli, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in Escherichia coli with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion E. coli expression vectors include pTrc (Amrann et al., (1988) Gene 69:301-315) and pET lid (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast Saccharomyces cerevisiae include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Luckow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Haloarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azoarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*. In some embodiments, one or more vectors driving expression of one or more elements of a CRISPR system (such as the Cas and/or the RNA guiding the Cas to a genomic target locus in a eukaryotic cell as referred to herein elsewhere) are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a Cas and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the Cas, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these.

When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a Cas protein. Cas protein or Cas mRNA or CRISPR guide RNA or RNA(s) can be delivered separately; and advantageously at least one of these is delivered via a nanoparticle complex. Cas mRNA can be delivered prior to the guide RNA to give time for Cas to be expressed. Cas mRNA might be administered 1-12 hours (preferably around 2-6 hours) prior to the administration of guide RNA. Alternatively, Cas mRNA and guide RNA can be administered together. Advantageously, a second booster dose of guide RNA can be administered 1-12 hours (preferably around 2-6 hours) after the initial administration of Cas mRNA+guide RNA. Additional administrations of Cas mRNA and/or guide RNA might be useful to achieve the most efficient levels of genome modification.

In certain embodiments, a Cas and/or an RNA capable of guiding the Cas to a target locus (i.e. guide RNA) as described herein elsewhere is delivered to or introduced in a cell, such as a eukaryotic cell. Conventional viral and non-viral based gene transfer methods can be used to introduce nucleic acids in cells. Non-viral vector delivery systems include DNA plasmids, RNA (e.g. a transcript of a vector described herein), naked nucleic acid, and nucleic acid complexed with a delivery vehicle, such as a liposome. Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). Viral vector delivery systems include DNA and RNA viruses, which have either episomal or integrated genomes after delivery to the cell. Viral vectors can be used to treat cells in vitro, and the modified cells can then be administered to a eukaryote, such as a non-human eukaryote. Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues. The tropism of a retrovirus can be altered by incorporating foreign envelope proteins, expanding the potential target population of target cells. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors that may be used in the practice of the invention include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). Zou et al. administered about 10 µl of a recombinant lentivirus having a titer of 1×109 transducing units (TU)/ml by an intrathecal catheter. These sorts of dosages can be adapted or extrapolated to use of a retroviral or lentiviral vector in the present invention.

If a Cas transgenic cell provided for herein is used (such as a eukaryotic cell), then only delivery of guide(s) is necessary, i.e. RNA capable of guiding Cas to a target locus. In some embodiments, one or more vectors described herein are used to produce a transgenic Cas organism, such as a non-human transgenic Cas organism, e.g., animal, mammal, primate, rodent, mouse, rat, rabbit. In some embodiments, the transgenic animal is a mammal, such as a mouse, rat, or rabbit. Guides or RNA(s) can be delivered via the same vector types as Cas. When both guides or RNA(s) and Cas are being delivered a dual-vector system where the Cas is delivered via in vivo expression from an AAV vector and the guide(s) are delivered by a separate AAV vector. This can be done substantially contemporaneously (i.e., co-delivery), but it could also be done at separate points in time, separated even by weeks or months. Of course, the ultimate separation is where the transgenic Cas organism is generated and thereafter the guide(s) or RNA(s) are delivered. Alternatively a first round of CRISPR-Cas systems can be delivered, and subsequently further guides or RNA(s) are delivered as the original Cas is still functional in the target cells may be re-used. If the Cas is under the control of an inducible promoter, then induction of transcription of new Cas in the target cells is preferred.

Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Accordingly, AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA. There are a number of ways to produce rAAV, and the invention provides rAAV and methods for preparing rAAV. For example, plasmid(s) containing or consisting essentially of the desired viral construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to Three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by a method that comprises or consists essentially of: infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or infecting susceptible cells with a rAAV containing exogenous DNA including DNA for expression, wherein the recombinant lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant lacks functioning cap and/or rep, wherein said cells supply cap and/or rep function that the recombinant lacks; or transfecting the susceptible cells with an AAV lacking functioning cap and/or rep and plasmids for inserting exogenous DNA into the recombinant so that the exogenous DNA is expressed by the recombinant and for supplying rep and/or cap functions whereby transfection results in an rAAV containing the exogenous DNA including DNA for expression that lacks functioning cap and/or rep. The rAAV can be from an AAV as herein described, and advantageously can be an rAAV1, rAAV2, AAV5 or rAAV having hybrid or capsid which may comprise AAV1, AAV2, AAV5 or any combination thereof. One can select the AAV of the rAAV with regard to the cells to be targeted by the rAAV. In addition to 293 cells, other cells that can be used in the practice of the invention and the relative infectivity of certain AAV serotypes in vitro as to these cells; see Grimm, D. et al, J. Virol. 82: 5887-5911 (2008) The invention provides rAAV that contains or consists essentially of an exogenous nucleic acid molecule encoding a CRISPR (Clustered Regularly Interspaced Short Palindromic Repeats) system or component(s) or coding therefor, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn).

AAV has a packaging limit of 4.5 or 4.75 Kb. This means that Cas as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

TABLE 1

| Species | Cas9 Size |
|---|---|
| Corynebacter diphtheria | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |

TABLE 1-continued

| Species | Cas9 Size |
|---|---|
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

The invention also can be practiced with an adenovirus vector, e.g., an E1-, partial E3-E4-deleted adenoviral vector may be used in the practice of the invention. Such vectors are safe as twenty-eight patients with advanced neovascular age-related macular degeneration (AMD) were given a single intravitreous injection of an E1-, partial E3-, E4-deleted adenoviral vector expressing human pigment epithelium-derived factor (AdPEDF.ll) (see, e.g., Campochiaro et al., Human Gene Therapy 17:167-176 (February 2006)); and previous adenovirus doses ranging from 106 to 109.5 particle units (PU) can be adapted to or employed in the practice of the instant invention (see, e.g., Campochiaro et al., Human Gene Therapy 17:167-176 (February 2006)). Adenoviral vector-mediated RNA transfer appears to be a viable approach for delivery of RNA(S). For adenoviral vector injections into a rat, 2×109 infectious particles were injected in 3 ml of normal saline solution (NSS). This can be adapted to or extrapolated from in the practice of the present invention. For siRNA, a rat was injected into the great saphenous vein with 12.5 µg of a siRNA and a primate was injected into the great saphenous vein with 750 µg of a siRNA. This can be adapted to or extrapolated from in the practice of the present invention.

In certain embodiments the Cas and/or RNA capable of guiding Cas to a target locus may be delivered by lentiviral delivery systems. Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 µg of lentiviral transfer plasmid (pCasES10) and the following packaging plasmids: 5 µg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4 C. They were then aliquoted and immediately frozen at −80° C.

Also useful in the practice of the invention is a minimal non-primate lentiviral vector, such as a lentiviral vector based on the equine infectious anemia virus (EIAV) (see, e.g., Balagaan, J Gene Med 2006; 8: 275 285, Published online 21 Nov. 2005 in Wiley InterScience (interscience.wiley.com). DOI: 10.1002/jgm.845). The vectors may have cytomegalovirus (CMV) promoter driving expression of the target gene. Intracameral, subretinal, intraocular and intravitreal injections are all within the ambit of the instant invention (see, e.g., Balagaan, J Gene Med 2006; 8: 275 285, Published online 21 Nov. 2005 in Wiley InterScience (interscience.wiley.com). DOI: 10.1002/jgm.845). In this regard, mention is made of RetinoStat®, an equine infectious anemia virus-based lentiviral gene therapy vector that expresses angiostatic proteins endostain and angiostatin that is delivered via a subretinal injection for the treatment of the web form of age-related macular degeneration is also contemplated (see, e.g., Binley et al., HUMAN GENE THERAPY 23:980-991 (September 2012)). Such a vector may be modified for practice of the present invention. Dosing of RetinoStat® (e.g., 1.1×105 transducing units per eye (TU/eye) in a total volume of 100 l) can be applied or extrapolated from in practicing the present invention with a lentivirus.

In certain embodiments, use is made of self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used and/or adapted to the CRISPR-Cas system of the present invention. A minimum of 2.5×106 CD34+ cells per kilogram patient weight may be collected and prestimulated for 16 to 20 hours in X-VIVO 15 medium (Lonza) containing 2 µmol/L-glutamine, stem cell factor (100 ng/ml), Flt-3 ligand (Flt-3L) (100 ng/ml), and thrombopoietin (10 ng/ml) (CellGenix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin, Takara Bio Inc.).

Accordingly, the invention contemplates amongst vector(s) useful in the practice of the invention: viral vectors, including retroviral vectors, lentiviral vectors, adenovirus vectors, or AAV vectors.

The Cas, for instance a Cas9, and/or any of the present RNAs, for instance a guide RNA, can also be delivered in the form of RNA. Cas mRNA can be generated using in vitro transcription. For example, Cas mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

Several types of particle and nanoparticle delivery systems and/or formulations are known to be useful in a diverse spectrum of biomedical applications; and particle and nanoparticle delivery systems in the practice of the instant invention can be as in WO 2014/093622 (PCT/US13/74667). In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm. As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm. Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., Cas enzyme or mRNA or guide RNA, or any combination thereof, and may include additional carriers and/or excipients) to provide particles of an optimal size for delivery according to certain embodiments of the present invention. In certain preferred embodiments, particle dimension (e.g., diameter) characterization is based on measurements using dynamic laser scattering (DLS). Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

In general, a "nanoparticle" refers to any particle having a diameter of less than 1000 nm. In certain preferred embodiments, nanoparticles have a greatest dimension (e.g., diameter) of 500 nm or less. In other preferred embodiments, nanoparticles have a greatest dimension ranging between 25 nm and 200 nm. In other preferred embodiments, nanoparticles have a greatest dimension of 100 nm or less. In other preferred embodiments, nanoparticles have a greatest dimension ranging between 35 nm and 60 nm. Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

With regard to nanoparticles that can deliver RNA, see, e.g., Alabi et al., Proc Natl Acad Sci USA. 2013 August 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93. Lipid Nanoparticles, Spherical Nucleic Acid (SNA™) constructs, nanoplexes and other nanoparticles (particularly gold nanoparticles) are also contemplate as a means for delivery of CRISPR/Cas system or component(s) thereof or vector(s) to intended targets. Particles, nanoparticles, and the like and vectors are advantageous for delivering the RNA(s) of the CRISPR-Cas system and particles and nanoparticles and the like may be advantageous for delivery of vector containing nucleic acid(s) encoding or comprising RNA(s) of the invention. In certain instances, e.g., where Cas is constitutively or inducibly or conditionally expressed by an organism or cells thereof, it is useful to deliver the RNA(s) (also herein sometimes termed "guides") of the CRISPR-Cas system separately from the Cas. It is considered as advantageous that the Cas may be delivered via a viral vector or be constitutively or inducibly or conditionally expressed and that guides specific to genomic targets are delivered separately. A recent publication, entitled "In vivo endothelial siRNA delivery using polymeric nanoparticles with low molecular weight" by James E. Dahlman and Carmen Barnes et al. Nature Nanotechnology (2014) published online 11 May 2014, doi:10.1038/nnano.2014.84, incorporated herein in its entirety, showed that polymeric nanoparticles made of low-molecular-weight polyamines and lipids can deliver siRNA to endothelial cells with high efficiency, thereby facilitating the simultaneous silencing of multiple endothelial genes in vivo. The authors reported that unlike lipid or lipid-like nanoparticles, the nanoparticle formulation they used (termed 7C1), differed from traditional lipid-based nanoparticle formulations because it can deliver siRNA to lung endothelial cells at low doses without substantially reducing gene expression in pulmonary immune cells, hepatocytes or peritoneal immune cells. The study further demonstrated that 7C1-mediated endothelial gene silencing affects function in vivo, by using the nanoformulation to modify mouse models of vascular permeability, emphysema, lung tumor growth and lung metastasis.

In some embodiments, the Cas is part of a fusion protein (i.e. chimeric protein) comprising one or more heterologous protein domains (e.g. about or more than about 1, 2, 3, 4, 5, 6, 7, 8, 9, 10, or more domains in addition to the Cas). A Cas fusion protein may comprise any additional protein sequence, and optionally a linker sequence between any two domains. Examples of protein domains that may be fused to a Cas include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. In such embodiments, it is preferred that Cas itself is catalytically inactive, or partially catalytically inactive. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A Cas may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) VP16 protein fusions. Additional domains that may form part of a fusion protein comprising a Cas are described in US20110059502, incorporated herein by reference. In some embodiments, a tagged Cas is used to identify the location of a target sequence. In certain embodiments, Cas is fused to a heterologous protein capable of manipulating a target sequence. By manipulation of a target sequence, Applicants mean the alteration of the target sequence, which may include the epigenetic manipulation of a target sequence. This epigenetic manipulation may be of the chromatin state of a target sequence, such as by modification of the methylation state of the target sequence (i.e. addition or removal of methylation or methylation patterns or CpG islands), histone modification, increasing or reducing accessibility to the target sequence, or by promoting 3D folding.

In some embodiments, a Cas sequence and/or RNA capable of guiding Cas (i.e. guide RNA) to a target locus may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the Cas sequence and/or RNA capable of guiding Cas to a genomic target locus may be a part of a Light Inducible Transcriptional Effector (LITE) to direct changes in transcriptional activity in a sequence-specific manner. The components of a LITE may include a Cas sequence and/or RNA capable of guiding Cas to a genomic target locus, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

In certain embodiments, the cells comprising the CRISPR-Cas system as described herein may be introduced in an organism, such as preferably an non-human organism. "introducing a cell in an organism" generally refers to transplanting or grafting cells, such as eukaryotic cells in an organism, such as a non-human organism, such as a non-human eukaryote.

Typically, cells in a suitable carrier or medium are injected in the animal at a desired site, such as without limitation subdermal, intradermal, transdermal, intracavernous, intravitreal, intra-articular, transscleral, intracerebral, intrathecal, epidural, intramuscular, intravenous, intracardiac, intraosseous, intraperitoneal, etc. the amount and concentration of cells to be injected may vary, but typically the amount of injected cells will be between $10^2$ to $10^{10}$ or between $10^2$ to $10^9$, or between $10^3$ to $10^{10}$ or between $10^3$ to $10^9$, or between $10^4$ to $10^{10}$ or between $10^4$ to $10^9$, such as between $10^4$ and $10^8$, or between $10^5$ and $10^7$, e.g., about $1\times10^5$, about $5\times10^5$, about $1\times10^6$, about $5\times10^6$, about $1\times10^7$, about $5\times10^7$, about $1\times10^8$, about $5\times10^8$, about $1\times10^9$, about $2\times10^9$, about $3\times10^9$, about $4\times10^9$, about $5\times10^9$, about $6\times10^9$, about $7\times10^9$, about $8\times10^9$, about $9\times10^9$ or about $1\times10^{10}$ cells per injection site. For example, such number of cells may particularly refer to the total number of cells to be administered to a non-human eukaryote, which administration may be suitably distributed over one or more doses (e.g., distributed over 2, 3, 4, 5, 6, 7, 8 9 or 10 or more doses) administered over one or more days (e.g., over 1, 2, 3, 4 or 5 or more days). Suitably, in a composition to be administered, cells may be present at a concentration between about $10^4$/ml to about $10^8$/ml, preferably between about $10^5$/ml and about $10^7$/ml, yet more preferably between about $1\times10^6$/ml and about $1\times10^7$/ml, such as, e.g., about $5\times10^6$/ml.

In one aspect, the invention provides for methods as described herein, which may be in vivo, ex vivo or in vitro methods. In some embodiments, the method comprises sampling a cell or population of cells from a human or non-human animal, and modifying the cell or cells as described herein. Culturing may occur at any stage ex vivo. The cell or cells may even be re-introduced into the non-human animal or plant. For re-introduced cells it is particularly preferred that the cells are stem cells.

For example, the recombinant cells as described herein may be used to create a non-human eukaryote, e.g., an animal, mammal, primate, rodent or cell that comprises a cell or a plurality of cells according to the invention as described herein elsewhere. The cell may be in vivo or ex vivo in the cases of multicellular organisms. In the instance where the cell is in culture (i.e. in vitro), a cell line may be established if appropriate culturing conditions are met and preferably if the cell is suitably adapted for this purpose (for instance a stem cell). Hence, cell lines are also envisaged. In some methods, the non-human eukaryote can be used to record gene expression in an in vivo context.

In an aspect the invention involves cells, e.g., non-human eukaryotic, e.g., animal, such as mammal, e.g., primate, rodent, mouse, rat, rabbit, etc. as described herein elsewhere, or even human cells, containing Cas polypeptide or transformed to constitutively express or alternatively inducibly and/or conditionally express Cas, e.g., such cells as to which a vector that contains nucleic acid molecule(s) encoding a Cas, e.g., with nucleic acid(s) encoding a promoter and preferably at least one NLS, advantageously two or more NLSs, or such cells that have had their genome altered, e.g., through the vector being an integrating virus or through such cells being stem cells or cells that give rise to a cell line or a living organism (but wherein such an organism is advantageously non-human), that contains and expresses nucleic acid molecule(s) encoding Cas. To these cells is then administered (simultaneously or subsequently) nucleic acids encoding guide RNA(s), e.g., AAV, adenovirus, lentivirus containing or providing RNA(s) that guide Cas to a target locus, e.g., under the control of a promoter of one or more gene of interest and/or particle(s) and/or nanoparticle(s) containing the nucleic acids encoding guide RNA(s), whereby the guide RNA(s) direct the Cas in the cells to provide a mutation in a selected target DNA sequence, or a plurality of mutation(s) such as from 3 to 50 mutations. Such cells may then be transplanted into or onto a eukaryote, such as an animal suitable for being a disease model, e.g., a rodent such as a mouse (see, e.g., literature on mouse transplantation cancer models, generally discussed at the NIH website; see emice.nci.nih.gov/aam/mouse/transplantation-mouse-models-1), chickens or chicken embryo or chicken embryo membrane (Kuzminien et al, "Evaluation of the Chicken Embryo chorioallantoic membrane Model for Laryngeal Tumor Transplantation," Papers on Anthropology XX, 2011, pp. 229-240), zebra fish (see, e.g., Haldi et al, "Human melanoma cells transplanted into zebrafish proliferate, migrate, produce melanin, form masses and stimulate angiogenesis in zebrafish," Angiogenesis. 2006; 9(3):139-51. Epub 2006 Oct. 19)).

The non-human eukaryote, e.g., animal model can then be used for testing, e.g., as to potential therapy and/or putative treatment via a possibly pharmaceutically active compound, while at the same time recording cellular events or cellular history. The administering of such compound can be at or to or for body delivery to the proliferated heterologous transplanted cells, e.g., direct injection at or near such proliferated heterologous transplanted cells, or injection or other administration in such a way that the compound is delivered into the heterologous transplanted cells, e.g., injection into the bloodstream whereby bodily functions transport to the proliferated heterologous transplanted cells. In an aspect of the invention, barcoding techniques of WO/2013/138585 A1 can be adapted or integrated into the practice of the invention.

With respect to use of the CRISPR-Cas system generally, mention is made of the documents, including patent applications, patents, and patent publications cited throughout this disclosure as embodiments of the invention can be used as in those documents. CRISPR-Cas system(s) (e.g., single or multiplexed) can be used in conjunction with recent advances in crop genomics. Such CRISPR-Cas system(s) can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. Such CRISPR-Cas system(s) can be used with regard to plants in Site-Directed Integration (SDI) or Gene Editing (GE) or any Near Reverse Breeding (NRB) or Reverse Breeding (RB) techniques. With respect to use of the CRISPR-Cas system in plants, mention is made of the University of Arizona website "CRISPR-PLANT" (genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi:10.1186/1746-4811-9-39); Brooks, "Efficient gene editing in tomato in the first generation using the CRISPR/Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi:10.1038/cr.2013.114; published online 20 Aug. 2013; Xie, "RNA-guided genome editing in plants using a CRISPR-Cas system," Mol Plant. 2013 November; 6(6):1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at newphytologist.com); Caliando et al, "Targeted DNA degradation using a CRISPR device stably carried in the host genome, NATURE COMMUNICATIONS 6:6989, DOI: 10.1038/ncomms7989, nature.com/naturecommunications DOI: 10.1038/ncomms7989; U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent. In an aspect, the invention provides kits containing any one or more of the elements discussed herein, such as one or more nucleic acid sequences encoding guide RNA(s) under suitable control of a promoter of a gene of interest, Cas protein, and/or recombinant cells as described herein. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises Cas (or a vector encoding Cas, or a Cas transgenic eukaryotic cell) and/or one or more, such as a library, oligonucleotides corresponding to a guide sequence for insertion into a vector (or vectors having already inserted such oligonucleotides) so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allow the provision of all elements of the systems of the invention. Kits can involve vector(s) and/or particle(s) and/or nanoparticle(s) containing or encoding RNA(s) to be administered to a eukaryotic cell, e.g., animal, mammal, primate, rodent, etc., with such a kit including instructions for administering to such a cell; and such a kit can optionally include a non-human eukaryote.

The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

It will be appreciated that where reference is made to a polynucleotide, where that polynucleotide is RNA and is said to 'comprise' a feature such as a tracr mate sequence, the RNA sequence includes the feature. Where the polynucleotide is DNA and is said to comprise a feature such as a tracr mate sequence, the DNA sequence is or can be transcribed into the RNA that comprises the feature at issue. Where the feature is a protein, such as the CRISPR enzyme, the DNA or RNA sequence referred to is, or can be, translated (and in the case of DNA transcribed first). Furthermore, in cases where an RNA encoding the CRISPR enzyme is provided to a cell, it is understood that the RNA is capable of being translated by the cell into which it is delivered.

As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" or "recombinant" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. The recombinant cells as described herein, therefore are engineered cells, or non-naturally occurring cells.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point (Tm). The Tm is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the Tm. In order to require at least about 70% nucleotide complementarity of hybridized sequences, moderately-stringent washing conditions are selected to be about 15 to 30° C. lower than the Tm. Highly permissive (very low stringency) washing conditions may be as low as 50° C. below the Tm, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4th Ed. —Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR.

In a preferred embodiment, single cells are sequenced to determine cellular events in single cells. Single-cell analysis may be performed using microfluidics. Microfluidics involves micro-scale devices that handle small volumes of fluids. Because microfluidics may accurately and reproducibly control and dispense small fluid volumes, in particular volumes less than 1 µl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947 and PCT publication No. WO2014085802 A1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to $10^8$ samples to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

The manipulation of fluids to form fluid streams of desired configuration, discontinuous fluid streams, droplets, particles, dispersions, etc., for purposes of fluid delivery, product manufacture, analysis, and the like, is a relatively

TABLE 2

| | Set | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S | well-studied art. Microfluidic systems have been described in a variety of contexts, typically in the context of miniaturized laboratory (e.g., clinical) analysis. Other uses have been described as well. For example, WO 2001/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Patent Application Publication No. 2014/0256595; and WO 2011/079176. In a preferred embodiment single cell analysis is performed in droplets using methods according to WO 2014085802. Each of these patents and publications is herein incorporated by reference in their entireties for all purposes.

Single cells of the present invention may be divided into single droplets using a microfluidic device. The single cells in such droplets may be further labeled with a barcode. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; Zheng, et al., 2016, "Haplotyping germline and cancer genomes with high-throughput linked-read sequencing" Nature Biotechnology 34, 303-311; and International patent publication number WO 2014210353 A2, all the contents and disclosure of each of which are herein incorporated by reference in their entirety.

Sequencing may include low pass targeted sequencing or high depth sequencing of transcriptomes and/or whole genomes or exomes. The term "depth (coverage)" as used herein refers to the number of times a nucleotide is read during the sequencing process. Depth can be calculated from the length of the original genome (G), the number of reads (N), and the average read length (L) as N×L/G. For example, a hypothetical genome with 2,000 base pairs reconstructed from 8 reads with an average length of 500 nucleotides will have 2× redundancy. This parameter also enables one to estimate other quantities, such as the percentage of the genome covered by reads (sometimes also called coverage). A high coverage in shotgun sequencing is desired because it can overcome errors in base calling and assembly. The subject of DNA sequencing theory addresses the relationships of such quantities. Even though the sequencing accuracy for each individual nucleotide is very high, the very large number of nucleotides in the genome means that if an individual genome is only sequenced once, there will be a significant number of sequencing errors. Furthermore rare single-nucleotide polymorphisms (SNPs) are common. Hence to distinguish between sequencing errors and true SNPs, it is necessary to increase the sequencing accuracy even further by sequencing individual genomes a large number of times.

The term "deep sequencing" as used herein indicates that the total number of reads is many times larger than the length of the sequence under study. The term "deep" as used herein refers to a wide range of depths greater than or equal to 1× up to 100×.

The terms "low-pass sequencing" or "shallow sequencing" as used herein refers to a wide range of depths less than or equal to 1×. In preferred embodiments depths are greater than or equal to 0.1× up to 0.5×.

The present invention may include barcoding. Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

The term "barcode" as used herein, refers to any unique, non-naturally occurring, nucleic acid sequence that may be used to identify the originating source of a nucleic acid fragment. Such barcodes may be sequences including but not limited to, about 20 base pair sequences. Although it is not necessary to understand the mechanism of an invention, it is believed that the barcode sequence provides a high-quality individual read of a barcode associated with a viral vector, labeling ligand, shRNA, sgRNA, cDNA, cell or nuclei, such that multiple species can be sequenced together.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western *Malagasy* Liotrigona Moure, 1961" African Invertebrates 51(2): 413-421 (2010); and Seberg et al., "How many loci does it take to DNA barcode a crocus?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequenceable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94). In one embodiment, the invention provides a method for preparing uniquely barcoded particles. Unique barcoded particles may be generated by a split pool method.

In certain embodiments, sequencing is performed using unique molecular identifiers (UMI). The term "unique molecular identifiers" (UMI) refers to a sequencing linker used in a method that uses molecular tags to detect and quantify unique amplified products. A UMI is used to distinguish effects through a single clone from multiple clones. In preferred embodiments, the amplification is by PCR. A sequencer linker with a random sequence of between 4 and 20 base pairs is added to the 5' end of the template, which is amplified and sequenced. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No: 11, 163-166). Not being bound by a theory, the UMI's are designed such that assignment to the original can take place despite up to 4-7 errors during amplification or sequencing.

In certain embodiments, multiple displacement amplification (MDA) is used. Multiple displacement amplification (MDA, is a non-PCR-based isothermal method based on the annealing of random hexamers to denatured DNA, followed by strand-displacement synthesis at constant temperature (Blanco et al. J. Biol. Chem. 1989, 264, 8935-8940). It has been applied to samples with small quantities of genomic DNA, leading to the synthesis of high molecular weight DNA with limited sequence representation bias (Lizardi et al. Nature Genetics 1998, 19, 225-232; Dean et al., Proc. Natl. Acad. Sci. U.S.A 2002, 99, 5261-5266). As DNA is synthesized by strand displacement, a gradually increasing number of priming events occur, forming a network of hyper-branched DNA structures. The reaction can be catalyzed by enzymes such as the Phi29 DNA polymerase or the large fragment of the Bst DNA polymerase. The Phi29 DNA polymerase possesses a proofreading activity resulting in error rates 100 times lower than Taq polymerase (Lasken et al. Trends Biotech. 2003, 21, 531-535).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

One or more plasmids containing CRISPR/Cas9 and/or guide RNA(s) of interest, driven by one or more promoter(s), are transfected, using methods known in the art, into one or more cells, mammalian or otherwise, native or expressing CRISPR/Cas9. Detection of promoter activity is achieved by examining the target site of the promoter-driven guide RNA. Co-amplification of cellular genetic material (e.g., cellular mRNA) is achieved using the same or differential priming simultaneously or sequentially following, for example, Shalek et al, Nature, 2013, Shalek et al, Nature, 2014, Trombetta et al, CPMB, 2014, or Macosko et al, Cell, 2015. The aggregate amplified product is examined using methods known to the art to assess promoter activation (read as successful CRISPR/Cas9 cuts) and the abundance of cellular genetic material (e.g., mRNA expression). This enables analysis of cellular genetic material guided by knowledge of previous cellular events.

Example 2

In another embodiment, the cut sites on a recorder DNA sequence of two or more promoter driven guides are constructed so as to overlap so that cut order and hence activation order can be assessed; targeting an independent DNA locus with the same or different RNA guides driven by a common promoter enables detection of inducer activity and temporal ordering. This allows assayed genetic information, such as mRNA expression, to be analyzed in light of cellular trajectory.

Example 3

In another example, the promoters used are inducible/repressable so that they can be specifically assayed within a user-defined time window by selectively providing the inducer (e.g., doxycycline) or removing the repressor. This enables genetic information, such as mRNA expression, to be analyzed based on the activity of a specific factor during an allotted time period.

Example 4

In another example, a reporter construct (e.g., a fluorescent protein) is used to denote cells that have expressed a guide RNA that encodes a cellular decision. Here, a nucleic acid construct, preferably a plasmid, is generated that contains a guide RNA for encoding a particular cellular event, such as Rorc activity in Cd4+ T cells, and a reporter such as GFP. Cells, e.g., primary mammalian mouse cells in vitro or in vivo, are transfected with this construct using any method known to the art, such as electroporation or via a viral vector, respectively. The transfected system is allowed to evolve in response to an external stimulus, such as anti-cd3/cd28 dynabeads and recombinant IL-6 & TGF-β, or naturally, respectively. After harvest from a petri dish or a tissue of interest, cells in which the factor, here Rorc, are active are detected and selected by FACS based on GFP fluorescence for downstream profiling, e.g., single cell RNA-Seq with primers for amplifying the guide RNA targeted DNA region, whether endogenous (e.g., the Rorc DNA locus) or introduced via a plasmid. In a single guide system, GFP detection enables assessment of the efficiency with which a signal is transduced into a change in DNA sequence (a hard coded memory); in a system with a few orthogonal reporters (e.g., GFP and RFP) and guides, it enables benchmarking of multiplexing; in a system with many guides (n) and a limited number of reporters (m<n), it enables the selection of cells in which an event of interest has occurred. A similar approach can be used to detect activity of a protein of interest (e.g., Rorc) within a time window of interest (e.g., 18-24 h), assuming that expression of the guide by that protein is selectively enabled by the introduction of an inducer or removal of a repressor during that time window. In other instances where the Cas9 and guide RNA constructs are physically distinct, the Cas9 construct may be labeled with a reporter to cells that express Cas9 as well. In other instances, human T cells are used in place of mouse T cells with a construct for human Rorc.

Example 5

In another example, a guide is used to detect plant cells into which a genetic modification has been introduced. Here, plant cells are transfected with a Cas9/guide system in which Cas9 is constitutively expressed and the recording guide, which targets Cas9 itself, is repressed by product of an unmodified gene. When a second guide is introduced that targets the gene of interest, Cas9 uses it to cut the gene of interest, resulting in a modified genetic product. This modified gene product, in turn, ceases to inactivate the Cas9-targeted guide expressed by the Cas9/guide system. This Cas9-targeting guide, with available Cas9 protein, can then destroy the Cas9 vector (self inactivation) to record the event and remove any unwanted side effects due to constitutive Cas9 expression. In another example, Cas9 destroys a modified gene of concern in a genetically modified strain before rendering itself inactivated.

Example 6

In another example, a series of different guides are used to record whether a particular sample, such as a plant, has been exposed to any agent of concern, such as a pesticide like DDT. Here, a guide construct responsive to the pesticide is made and introduced into a plant's cells. If that plant is exposed to a pesticide, it expresses a guide that modifies an endogenous DNA template that is retained during growth (e.g., cell proliferation). After harvest, a regulatory agency can test a sample of the plant to see if that pesticide was used by looking for modifications of the DNA target of the guide RNA. In another example, this system can be used in conjunction with a self-inactivation system or another inactivation system in which a second guide is activated by exogenous application of an agent to destroy the Cas9.

Example 7

In another example, the Cas9/reporter guides system is used to examine the activity of different transcription factors in differentiation mouse or human es cells or IPSCs. Here, guides targeting different endogenous DNA loci and driven by the activity of different transcription factors, such as Sox1 (Ectoderm), Brachyury (Mesoderm), Sox7 (Endoderm), are transfected into primary mouse or human ES cells or IPSCs. The system is guided to differentiate by the application or removal of chemicals in the cellular microenvironment. After a period of time, for example 7 days, cells are sorted based on early surface markers for each lineage and profiled to examine which set of transcription factors had been active inside of each of those cells. In this way, potential regulators identified through other profiling methods (e.g., RNA-Seq at multiple different time points) can be tested for their activity and specificity for a given lineage. In another example, the reporter guides are made inducible so that a researcher can look for the activity of a specific transcription factor (e.g., Sox1) within a specific window (e.g., 4-6 days).

Example 8

In another example, the Cas9/reporter guide system is made resettable by the use of two distinct guides that are sequentially linked in a single template and an inducible recombinase such as Bxb1 (ref Siuti, NBT, 31, 448, 2103). Here, a first guide is used to record exposure/activity in one specific DNA locus. At a latter time point, an inducer is added causing the recombinase to become expressed. By structuring the plasmid so that the first guide is flanked to the left by an attB site and to the right by a stop codon, an attP site, and a second guide, this recombinase can flip out the first guide and stop codon so that factor of interest now drives expression of a second guide that can target an independent endogenous DNA locus to record future transcription factor activity. In another version, several guides are thusly chained using orthogonal recombinase sites (e.g., those from Bxb1 and phiC31) to enable multiple resettings. In another version, an inducer is instead used to generate a third guide that can target a repressor region preventing the second guide from being expressed; here, once induced, subsequent activity of the factor of interest can be followed by examining the endogenous DNA targets of the second guide.

Example 9

In another example, redundant encoding of guide RNAs responsive to a cellular activity is used. In order to test for dual-cleavage efficiency, applicants used single cells sorted from clones containing two gRNA constructs and Cas9. These clones contained gRNAs targeting either the Bmi1 and PHF8 loci or BRD4 and KDM4C. To test the efficacy of double cutting, Applicants developed an approach that used multiple displacement amplification (MDA) to amplify the genomic DNA of each single cell that were expected to present indels in BMI1 and PHF8 loci or BRD4 and KDM4C. Applicants then selectively enriched target cut-sites by PCR, before using a second, step-out PCR to append barcodes and Illumina sequencing adaptors (FIG. 10A).

Figure 10:
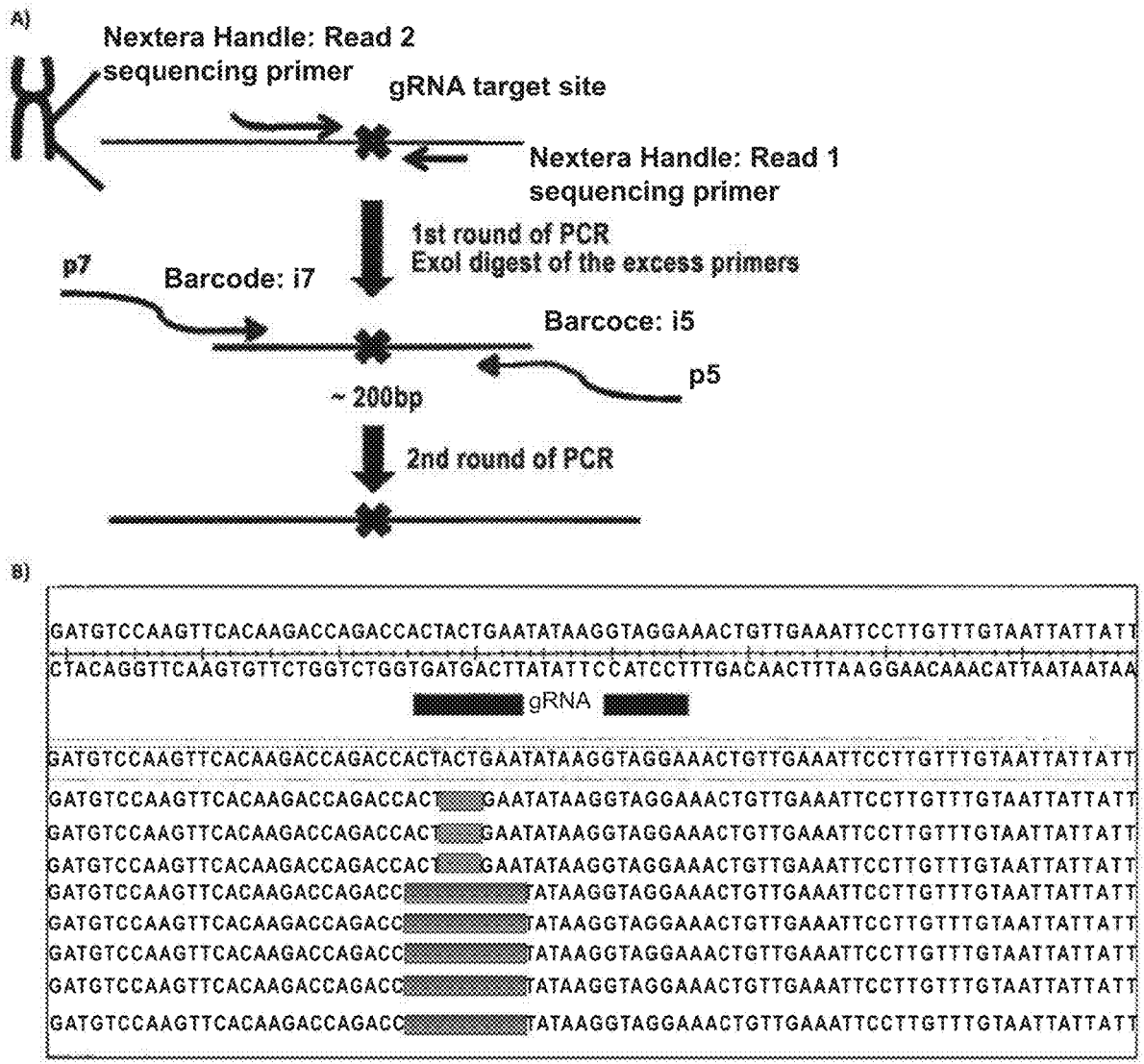
FIG. 10 illustrates Indel identification. (A) Indel amplification strategy. First, specific genomic sequences are enriched by PCR and then index (i5, i7, in green) and sequencing adaptors (p5, p7, in purple) are added with a step-out PCR. (B) Typical indel structure observed at the Bmi1 site in a single cell. Figure discloses SEQ ID NOS 35, 36, 35, 37, 37, 37, 38, 38, 38, 38, and 38, respectively, in order of appearance.

As Cas9 double stranded breaks are mainly repaired through non-homologous end joining (NHEJ), small indels errors (1-10 bp) are normally generated in the course of repair (FIG. 10B). From the sequencing data, Applicants found that as many as 75% and 80% of the single cells harbored an indel at their BMI1 and PHF8 target site, respectively; 100% of the cells had an indel in at least one of the two loci. Applicants also found that 20% and 88% of the single cells harbored an indel at their BRD4 and KDM4C target site, respectively; 91% of the cells had an indel in at least one of the two loci. The poor cut rate observed for BRD4 is consistent with previous studies and is probably due to a low on-target score/activity, suggesting the importance of proper sgRNA design for high-efficiency editing.

These results clearly demonstrate that CRISPR/Cas9 can be used to generate permanent DNA modifications that can be read at a later time point via next generation sequencing (NGS). By carefully designing our sgRNA, and using redundant encoding, especially important for DNA based readout—(multiple cuts per event) to reduce false negatives. Applicants can accurately identify any cell in which an event of interest (e.g., TF expression) has occurred.

Example 10

In another example, transcriptome amplification activity is used. An alternative strategy for profiling Cas9 edits is to amplify the transcriptomes of singles cells, rather than their genomes, and then selectively enrich the target cut sites. Sequencing of successful libraries yielded mostly wild type reads most likely due to mRNAs presenting an indel mutation being quickly degraded via non-sense mediated decay making detection of edits from the transcriptome alone difficult. Applicants can co-amplify the genome and the transcriptome in these kind of situations. Recently, methods for simultaneous amplification of the genome and transcriptome of a single cell have been described. Both rely on using an oligo-dT primer to separate mRNA from genomic DNA (gDNA); they differ in when they physically separate the mRNA from the gDNA. In the first, mRNA is tagged with a specific adaptor during RT, while the gDNA receive a different adaptor via a quasilinear amplification step following RT allowing gDNA and mRNA to be separately further amplified (Macaulay, I. C.; et al., Nature Methods 2015, 12, 519). The second approach uses oligo-dT primers attached to magnetic streptavidin beads via a biotin linker to pull out mRNA right after cell lysis and processes gDNA and mRNA separately (Dey, S. S.; et al., Nature Biotechnology 2015, 33, 285). In both strategies the genome can either be fully amplified using randomized primers or can be directly targeted to amplify the site of interest by designing targeting primers. Here having multiple transcripts that can be read reduces issues associated with protocol inefficiency. DNA can also support or replace RNA made measurements through using multiple DNA edits per events of the same or different varieties. This reduces the likelihood of false negatives.

Example 11

In another example, recombinase may be used to record cellular events. Here, a recombinase is placed under the control of a transcription factor of interest and the readout is inversion of the DNA sequence at fixed recombination site rather than an indel. To test this system, Applicants have designed plasmids that place a recombinase (φC31 or Bxb1) under the control of a dox-responsive promoter. On a second plasmid a reversed EF-1α promoter flanked by the recombinase attB and attP sites is followed by a RFP. Thus, upon dox activation, the recombinase reverses the promoter, enabling the RFP to be expressed by the cell. Applicants then image the cells and/or use FACS to check for recombination efficiency.

In preliminary tests, Applicants transiently transfected HEK293T cells with the prepared plasmids and immediately induced with 1 µg/mL doxycycline. Applicants imaged cells after 24 hours and was able to observe recombination events via imaging (i.e. cells that turned red) (FIG. 11). The frequency of recombination events was measured by flow cytometry (Table 1). The dox promoter appeared to be very leaky and the recombination efficiency was quite low. The leakiness can be controlled by switching to a promoter with tighter control. Recombination efficiency can compared to transfection efficiency using a GFP transfection control plasmid on top of the two inserted plasmid or an antibiotic selection marker. Recombination efficiency can also be improved by: (1) optimizing the recombinase sequence obtained for mammalian expression, and (2) adding a nuclear localization signal (NLS) at the end of the recombinase.

TABLE 3

% of RFP positive cells as measured by flow cytometry. All negative controls showed less than 1.5% of RFP positive cells.

| Recombinase | [Dox] | % of RFP positive cells |
| --- | --- | --- |
| Bxb1 | 1 µg/mL | 39% |
| Bxb1 | 0 µg/mL | 14% |
| φC31 | 1 µg/mL | 30% |
| φC31 | 0 µg/mL | 19% |

This experiment also shows that there is a real risk of having false positive because of promoter leakiness. Tet-inducible systems with better control can be used designed (Loew, R. et al., BMC Biotechnology 2010, 10, 1.

Example 12

In another example, gRNAs are designed for cellular recording. Guide RNAs are usually expressed under polIII promoters, but Applicants can utilize systems to have them controlled by polII promoters. In order to do this Applicants flank the gRNAs by two ribozymes (Hammerhead and HDV) based on previous studies (Nissim, L. et al., Mol Cell 2014, 54, 698; and Gao, Y. et al., Plant Biol 2014, 56, 343).

The invention is further described by the following numbered paragraphs:

1. A method of recording a cellular event in a cell and detecting the occurrence of the cellular event at a point of assay after the event has occurred comprising:
    (a) providing a cell comprising a CRISPR-Cas system, said CRISPR-Cas system comprising at least one guide RNA that targets a selected recorder DNA sequence and a Cas protein capable of modifying the selected recorder DNA sequence; whereby a nucleic acid molecule encoding at least one of said guide RNA or Cas protein is operably connected in the cell with a regulatory element comprising a promoter that is activated in parallel to the cellular event or as a consequence of the cellular event, and whereby expression of at least one CRISPR-Cas system component is driven by the promoter; and (b) detecting the occurrence of the cellular event based on detection of the modification of said selected recorder DNA sequence.

2. The method according to numbered paragraph 1, wherein the cellular event is a change in expression of a gene of interest, a change in level of a protein of interest, a change in the level of an intracellular molecule, a change in a posttranslational modification, a change in the activity of a factor of interest, a change in microenvironment, exposure to a molecule of interest, activation of a transcription factor, deactivation of a transcriptional repressor, recruitment of a transcription factor, activation of a signal transduction pathway, or remodeling of chromatin.

3. The method according to numbered paragraphs 1 or 2, wherein the promoter is a promoter of a gene of interest.

4. The method according to any of numbered paragraphs 1 to 3, wherein the promoter is responsive to a specific transcription factor.

5. The method according to numbered paragraph 4, wherein the transcription factor is recruited to the promoter as a result of activation of a signal transduction pathway.

6. The method of numbered paragraph 4, wherein the promoter is responsive to a nuclear receptor.

7. The method of numbered paragraph 2, wherein exposure to a factor of interest comprises exposure to a chemical, biochemical, signaling molecule, or pathogen.

8. The method according to any of numbered paragraphs 1 to 7, wherein said method further comprises introducing in said cell a vector comprising said selected recorder DNA sequence and said method comprises detection of the modification of said selected recorder DNA sequence on said vector.

9. The method according to any of numbered paragraphs 1 to 8, wherein said selected recorder DNA sequence is not endogenous to said cell.

10. The method according to any of numbered paragraphs 1 to 8, wherein said selected recorder DNA sequence is a sequence endogenous to said cell and selected based on its minimal impact on the functioning of the cell after modification by the CRISPR-Cas system.

11. The method according to any of numbered paragraphs 2 to 10, wherein said selected recorder DNA sequence is not comprised in said gene of interest.

12. The method according to any of numbered paragraphs 2 to 11, wherein said CRISPR-Cas system does not modify the expression of said gene of interest.

13. The method according to any of numbered paragraphs 1 to 12, wherein said CRISPR-Cas system is multiplexed.

14. The method according to any of numbered paragraphs 1 to 13, in which the cell encodes more than one guide RNA, whereby at least a first guide RNA targets a first selected recorder DNA sequence for determining a first cellular event and a second guide RNA targets a second selected recorder DNA sequence different from said first selected recorder DNA sequence for determining a second cellular event.

15. The method according to numbered paragraph 14, wherein said second selected recorder DNA sequence targeted by the second guide RNA provided for determining the said second cellular event is present in the cell only after said modification by said Cas protein of said first selected recorder DNA sequence provided for determining the said first cellular event.

16. The method according to numbered paragraph 14, wherein said second selected recorder DNA sequence targeted by the second guide RNA provided for determining the said second cellular event is present in the cell only before said modification by said Cas protein of said first selected recorder DNA sequence provided for determining the said first cellular event.

17. The method according to any of numbered paragraphs 1 to 16, wherein said modification of said selected recorder DNA sequence comprises inducing one or more mutations in said selected DNA recorder sequence.

18. The method according to any of numbered paragraphs 1 to 17, wherein said modification of said selected recorder DNA sequence comprises the introduction, deletion, or substitution of one or more nucleotides in said selected recorder DNA sequence.

19. The method of any of numbered paragraphs 1 to 18, wherein said modification comprises detection by DNA sequencing, PCR, hybridization, RFLP, or AFLP.

20. The method of any of numbered paragraphs 1 to 19, wherein said modification comprises detection by single cell PCR.

21. The method of any of numbered paragraphs 1 to 20, wherein said modification comprises detection by single cell DNA or RNA sequencing.

22. The method according to any of numbered paragraphs 1 to 21 which comprises, introducing into said cell a nucleic acid molecule encoding:
(A) a CRISPR-Cas system comprising a Cas protein and one or more guide RNAs that target said selected recorder DNA sequence, whereby the Cas protein modifies said selected DNA sequence; or
(B) either one of:
(a) one or more CRISPR-Cas system guide RNAs that hybridize with a selected DNA sequences, or
(b) a Cas protein.

23. The method according to any of numbered paragraphs 1 to 22, wherein said cell is a eukaryotic cell.

24. The method according to any of numbered paragraphs 1 to 23, wherein said guide RNA, said Cas protein, or both are conditionally and/or inducibly expressed in said cell.

25. The method according to any of numbered paragraphs 1 to 24, wherein said CRISPR-Cas system is self-inactivating.

26. The method according to any of numbered paragraphs 1 to 24, wherein said guide RNA comprises a guide sequence, a tracr mate sequence and a tracr sequence.

27. The method according to numbered paragraph 26, wherein said guide sequence and said tracr mate sequence are arranged in a 5' to 3' orientation on a single nucleic acid molecule.

28. The method according to numbered paragraph 26 or 27, wherein said guide sequence, said tracr mate sequence, and said tracr sequence are arranged in a 5' to 3' orientation on a single nucleic acid molecule.

29. The method according to any of numbered paragraphs 26 to 28, wherein when transcribed, the tracr mate sequence hybridizes to the tracr sequence and the guide sequence directs sequence-specific binding of a CRISPR complex to the target sequence,
wherein the CRISPR complex comprises the Cas complexed with (1) the guide sequence that is hybridized to the target sequence, and (2) the tracr mate sequence that is hybridized to the tracr sequence.

30. The method according to any of numbered paragraphs 1 to 29, wherein said guide RNA comprises a single guide RNA.

31. The method according to any of numbered paragraphs 1 to 30, wherein the guide RNA; or the tracr, tracr mate, and guide sequence together, comprise two or more hairpins.

32. The method according to any of numbered paragraphs 1 to 31, wherein said guide RNA, said Cas protein, or both are introduced into the cell by a delivery system comprising viral particles, liposomes, electroporation, microinjection or conjugation.

33. The method according to any of numbered paragraphs 1 to 32, wherein said guide RNA, said Cas protein, or both are introduced into said cell by means of transduction.

34. The method according to any of numbered paragraphs 1 to 33, wherein said guide, said Cas protein, or both are introduced into said cell by means of lentiviral, retroviral, adenoviral, or AAV transduction.

35. The method according to any of numbered paragraphs 1 to 34, wherein the Cas protein is codon optimized for expression in a eukaryotic cell.

36. The method according to any of numbered paragraphs 1 to 35, wherein said Cas is a type II Cas.

37. The method according to any of numbered paragraphs 1 to 36, wherein said Cas is Cas9.

38. The method according to any of numbered paragraphs 1 to 37, wherein said Cas is a Cas originating from *Streptococcus pyogenes*, *Streptococcus thermophiles*, or *Staphylococcus aureus*.

39. The method according to any of numbered paragraphs 1 to 38, wherein said Cas is a mutated Cas having an altered catalytic activity.

40. The method according to any of numbered paragraphs 1 to 39, wherein said Cas is a mutated Cas having a nickase activity.

41. The method according to any of numbered paragraphs 1 to 40, wherein said Cas comprises at least one or more nuclear localization sequences (NLSs).

42. The method according to any of numbered paragraphs 1 to 41, wherein said Cas comprises at least one or more nuclear localization sequences (NLSs) in the proximity of a terminus of the CRISPR enzyme.

43. The method according to any of numbered paragraphs 1 to 42, wherein the method is conducted in vivo in a non-human organism or ex vivo on a cell taken from said organism, optionally wherein said cell is returned to said organism.

44. A recombinant cell comprising one or more nucleic acid molecules encoding a CRISPR-Cas system comprising a guide RNA that targets a selected recorder DNA sequence and a Cas protein capable of modifying a targeted genomic locus, whereby at least one of said nucleic acid molecules encoding at least one of said guide RNA or Cas protein is operably connected with a regulatory element comprising a promoter that is activated in parallel to a cellular event or as a consequence of a cellular event.

45. The recombinant cell according to numbered paragraph 44, wherein the cellular event is a change in expression of a gene of interest, a change in level of a protein of interest, a change in the level of an intracellular molecule, a change in a posttranslational modification, a change in the activity of a factor of interest, a change in microenvironment, exposure to a molecule of interest, activation of a transcription factor, deactivation of a transcriptional repressor, recruitment of a transcription factor, activation of a signal transduction pathway, or remodeling of chromatin.

46. The recombinant cell according to numbered paragraph 44 or 45, wherein the promoter is a promoter of a gene of interest.

47. The recombinant cell according to any of numbered paragraphs 44 to 46, wherein the promoter is responsive to a specific transcription factor.

48. The recombinant cell according to numbered paragraph 47, wherein the transcription factor is recruited to the promoter as a result of activation of a signal transduction pathway.

49. The recombinant cell of numbered paragraph 47, wherein the promoter is responsive to a nuclear receptor.

50. The recombinant cell of numbered paragraph 45, wherein exposure to a factor of interest comprises exposure to a chemical, biochemical, signaling molecule, or pathogen.

51. The recombinant cell according to any of numbered paragraphs 44 to 50, wherein said selected recorder DNA sequence is not endogenous to said cell.

52. The recombinant cell according to any of numbered paragraphs 44 to 50, wherein said selected recorder DNA sequence is a sequence endogenous to said cell and selected based on its minimal impact on the functioning of the cell after modification by the CRISPR-Cas system.

53. The recombinant cell according to any of numbered paragraphs 45 to 52, whereby said selected recorder DNA sequence is not comprised in said gene of interest.

54. The recombinant cell according to any of numbered paragraphs 44 to 53, wherein said CRISPR-Cas system does not modify the expression of said gene of interest.

55. The recombinant cell according to any of numbered paragraphs 44 to 54, wherein said cell comprises, operably connected with a regulatory element comprising a promoter of a gene of interest, a nucleic acid molecule encoding either:
(A) a CRISPR-Cas system comprising a Cas protein and one or more guide RNAs that target said selected recorder DNA sequence, whereby the Cas protein modifies said selected recorder DNA sequence; or
(B) either one of:
(a) one or more CRISPR-Cas system guide RNAs that hybridize with a selected recorder DNA sequence, or
(b) a Cas protein; wherein said cell further comprises a guide RNA that targets said selected recorder DNA sequence.

56. The recombinant cell according to any of numbered paragraphs 44 to 55, wherein said cell is a eukaryotic cell.

57. The recombinant cell according to any of numbered paragraphs 44 to 56, wherein said guide RNA, said Cas protein, or both are capable of being conditionally and/or inducibly expressed in said cell.

58. The recombinant cell according to any of numbered paragraphs 44 to 57, wherein said CRISPR-Cas system is self-inactivating.

59. The recombinant cell according to any of numbered paragraphs 44 to 58, wherein said guide RNA comprises a guide sequence, a tracr mate sequence and a tracr sequence.

60. The recombinant cell according to numbered paragraph 59, wherein said guide sequence and said tracr mate sequence are arranged in a 5' to 3' orientation on a single nucleic acid molecule.

61. The recombinant cell according to numbered paragraph 59 or 60, wherein said guide sequence, said tracr mate sequence, and said tracr sequence are arranged in a 5' to 3' orientation on a single nucleic acid molecule.

62. The recombinant cell according to any of numbered paragraphs 59 to 61, wherein when transcribed, the tracr mate sequence hybridizes to the tracr sequence and the guide sequence directs sequence-specific binding of a CRISPR complex to the target sequence,
wherein the CRISPR complex comprises the Cas complexed with (1) the guide sequence that is hybridized to the target sequence, and (2) the tracr mate sequence that is hybridized to the tracr sequence.

63. The recombinant cell according to any of numbered paragraphs 44 to 62, wherein said guide RNA comprises a single guide RNA.

64. The recombinant cell according to any of numbered paragraphs 44 to 63, wherein the guide RNA; or the tracr, tracr mate, and guide sequence together, comprise two or more hairpins.

65. The recombinant cell according to any of numbered paragraphs 44 to 64, wherein a nucleic acid encoding said guide RNA, said Cas protein, or both is genomically integrated in said cell.

66. The recombinant cell according to any of numbered paragraphs 44 to 65, wherein a nucleic acid encoding said guide RNA, said Cas protein, or both is extra-chromosomal in said cell.

67. The recombinant cell according to any of numbered paragraphs 44 to 66, wherein the Cas protein is codon optimized for expression in a eukaryotic cell.

68. The recombinant cell according to any of numbered paragraphs 44 to 67, wherein said Cas is a type II Cas.

69. The recombinant cell according to any of numbered paragraphs 44 to 68, wherein said Cas is Cas9.

70. The recombinant cell according to any of numbered paragraphs 44 to 69, wherein said Cas is a Cas originating from *Streptococcus pyogenes, Streptococcus* thermophiles, or *Staphylococcus aureus*.

71. The recombinant cell according to any of numbered paragraphs 44 to 70, wherein said Cas is a mutated Cas having an altered catalytic activity.

72. The recombinant cell according to any of numbered paragraphs 44 to 71, wherein said Cas is a mutated Cas having a nickase activity.

73. The recombinant cell according to any of numbered paragraphs 44 to 72, wherein said Cas comprises at least one or more nuclear localization sequences (NLSs).

74. The recombinant cell according to any of numbered paragraphs 44 to 73, wherein said Cas comprises at least one or more nuclear localization sequences (NLSs) in the proximity of a terminus of the CRISPR enzyme.

75. A kit comprising the recombinant cell according to any of numbered paragraphs 44 to 74.

76. The kit according to numbered paragraph 61, further comprising instructions for performing the method according to any of numbered paragraphs 1 to 36.

77. A non-human organism comprising the recombinant cell according to any of numbered paragraphs 44 to 74.

78. The non-human organism according to numbered paragraph 77, wherein said organism is a eukaryotic organism.

79. The non-human organism according to numbered paragraph 77 or 78, wherein said organism is a plant or animal organism.

80. The non-human organism according to any of numbered paragraphs 77 to 79, wherein said organism is a mammal.

81. The at least one guide RNA according to any of the preceding numbered paragraphs, wherein two or more guide RNAs are operably connected with a regulatory element comprising a promoter that is activated in parallel to a cellular event or as a consequence of a cellular event and wherein each guide RNA is specific for a different recorder DNA sequence, whereby upon the cellular event at least one recorder DNA sequence is modified.

82. The at least one guide RNA according to any of the preceding numbered paragraphs, wherein two or more guide RNAs are specific for targeting the same recorder DNA sequence.

83. The regulatory element comprising a promoter according to any of the preceding numbered paragraphs, wherein said promoter is an RNA polymerase II (pol II) promoter.

84. The at least one guide RNA according to numbered paragraph 83, wherein said guide RNA is flanked by two ribozymes.

85. A method of recording a cellular event in a cell and detecting the occurrence of the cellular event at a point of assay after the event has occurred comprising:
 (a) providing a cell comprising a recombinase operably connected in the cell with a regulatory element comprising a promoter that is activated in parallel to the cellular event or as a consequence of the cellular event, and a recorder DNA sequence comprising recombination sites for said recombinase, whereby expression of the recombinase is driven by the promoter; and
 (b) detecting the occurrence of the cellular event based on detection of the recombination of said recorder DNA sequence.

86. The method according to numbered paragraph 85, wherein the recorder DNA sequence comprises a reversed promoter and recombination of the reversed promoter activates expression of a detectable reporter molecule.

87. The method according to numbered paragraph 86, wherein the cellular event is coupled to a single cell genomic readout.

88. A recombinant cell comprising a nucleic acid molecule encoding a recombinase operably connected with a regulatory element comprising a promoter that is activated in parallel to a cellular event or as a consequence of a cellular event and a recorder DNA sequence comprising recombination sites for said recombinase.

REFERENCES

Aceto, N., Bardia, A., Miyamoto, D. T., Donaldson, M. C., Wittner, B. S., Spencer, J. A., Yu, M., Pely, A., Engstrom, A., Zhu, H., et al. (2014). Circulating tumor cell clusters are oligoclonal precursors of breast cancer metastasis. Cell 158, 1110-1122.

Bell, C. L., Vandenberghe, L. H., Bell, P., Limberis, M. P., Gao, G. P., Van Vliet, K., Agbandje-McKenna, M., and Wilson, J. M. (2011). The AAV9 receptor and its modification to improve in vivo lung gene transfer in mice. The Journal of clinical investigation 121, 2427-2435.

Chen, S., Xue, Y., Wu, X., Le, C., Bhutkar, A., Bell, E. L., Zhang, F., Langer, R., and Sharp, P. A. (2014). Global microRNA depletion suppresses tumor angiogenesis. Genes & development 28, 1054-1067.

Bibikova, M., Beumer, K., Trautman, J. K., and Carroll, D. (2003). Enhancing gene targeting with designed zinc finger nucleases. Science 300, 764.

Cerami, E., Gao, J., Dogrusoz, U., Gross, B. E., Sumer, S. O., Aksoy, B. A., Jacobsen, A., Byrne, C. J., Heuer, M. L., Larsson, E., et al. (2012). The cBio cancer genomics portal: an open platform for exploring multidimensional cancer genomics data. Cancer discovery 2, 401-404.

Chen, S., Xue, Y., Wu, X., Le, C., Bhutkar, A., Bell, E. L., Zhang, F., Langer, R., and Sharp, P. A. (2014). Global microRNA depletion suppresses tumor angiogenesis. Genes & development 28, 1054-1067.

Cheng, Z., Ma, R., Tan, W., and Zhang, L. (2014). MiR-152 suppresses the proliferation and invasion of NSCLC cells by inhibiting FGF2. Experimental & molecular medicine 46, el 12.

Chung, J., Issadore, D., Ullal, A., Lee, K., Weissleder, R., and Lee, H. (2013). Rare cell isolation and profiling on a hybrid magnetic/size-sorting chip. Biomicrofluidics 7, 54107.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Deltcheva, E., Chylinski, K., Sharma, C. M., Gonzales, K., Chao, Y., Pirzada, Z. A., Eckert, M. R., Vogel, J., and Charpentier, E. (2011). CRISPR RNA maturation by trans-encoded small RNA and host factor RNase III. Nature 471, 602-607.

Dull, T., Zufferey, R., Kelly, M., Mandel, R. J., Nguyen, M., Trono, D., and Naldini, L. (1998). A third-generation lentivirus vector with a conditional packaging system. Journal of virology 72, 8463-8471.

DuPage, M., Dooley, A. L., and Jacks, T. (2009). Conditional mouse lung cancer models using adenoviral or lentiviral delivery of Cre recombinase. Nature protocols 4, 1064-1072.

Francia, G., Cruz-Munoz, W., Man, S., Xu, P., and Kerbel, R. S. (2011). Mouse models of advanced spontaneous metastasis for experimental therapeutics. Nature reviews Cancer 11, 135-141.

Frese, K. K., and Tuveson, D. A. (2007). Maximizing mouse cancer models. Nature reviews Cancer 7, 645-658.

Gasiunas, G., Barrangou, R., Horvath, P., and Siksnys, V. (2012). Cas9-crRNA ribonucleoprotein complex mediates specific DNA cleavage for adaptive immunity in bacteria. Proceedings of the National Academy of Sciences of the United States of America 109, E2579-2586.

Gao, J., Aksoy, B. A., Dogrusoz, U., Dresdner, G., Gross, B., Sumer, S. O., Sun, Y., Jacobsen, A., Sinha, R., Larsson, E., et al. (2013). Integrative analysis of complex cancer genomics and clinical profiles using the cBioPortal. Science signaling 6, p 11.

Gilbert, L. A., Horlbeck, M. A., Adamson, B., Villalta, J. E., Chen, Y., Whitehead, E. H., Guimaraes, C., Panning, B., Ploegh, H. L., Bassik, M. C., et al. (2014). Genome-Scale CRISPR-Mediated Control of Gene Repression and Activation. Cell.

Govindan, R., Ding, L., Griffith, M., Subramanian, J., Dees, N. D., Kanchi, K. L., Maher, C. A., Fulton, R., Fulton, L., Wallis, J., et al. (2012). Genomic landscape of non-small cell lung cancer in smokers and never-smokers. Cell 150, 1121-1134.

Halbert, C. L., Allen, J. M., and Miller, A. D. (2002). Efficient mouse airway transduction following recombination between AAV vectors carrying parts of a larger gene. Nature biotechnology 20, 697-701.

Hegi, M. E., Diserens, A. C., Gorlia, T., Hamou, M. F., de Tribolet, N., Weller, M., Kros, J. M., Hainfellner, J. A., Mason, W., Mariani, L., et al. (2005). MGMT gene silencing and benefit from temozolomide in glioblastoma. The New England journal of medicine 352, 997-1003.

Heimann, R., and Hellman, S. (1998). Aging, progression, and phenotype in breast cancer. Journal of clinical oncology: official journal of the American Society of Clinical Oncology 16, 2686-2692.

Herbig, E., Warfield, L., Fish, L., Fishburn, J., Knutson, B. A., Moorefield, B., Pacheco, D., and Hahn, S. (2010). Mechanism of Mediator recruitment by tandem Gcn4 activation domains and three Gal11 activator-binding domains. Molecular and cellular biology 30, 2376-2390.

Herbst, R. S., Heymach, J. V., and Lippman, S. M. (2008). Lung cancer. The New England journal of medicine 359, 1367-1380.

Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nature biotechnology 31, 827-832.

Hsu, P. D., Lander, E. S., and Zhang, F. (2014). Development and applications of CRISPR-Cas9 for genome engineering. Cell 157, 1262-1278.

Huang, S., Holzel, M., Knijnenburg, T., Schlicker, A., Roepman, P., McDermott, U., Garnett, M., Grernrum, W., Sun, C., Prahallad, A., et al. (2012). MED12 controls the response to multiple cancer drugs through regulation of TGF-beta receptor signaling. Cell 151, 937-950.

Ioannidis John, P. A., Castaldi P., Evangelou E. A compendium of genome-wide associations for cancer: critical synopsis and reappraisal. J. Natl Cancer Inst 2010; 102: 846-858.

Iwasaki, M., Homma, S., Hishiya, A., Dolezal, S. J., Reed, J. C., and Takayama, S. (2007). BAG3 regulates motility and adhesion of epithelial cancer cells. Cancer research 67, 10252-10259.

Jasin, M., de Villiers, J., Weber, F., and Schaffner, W. (1985). High frequency of homologous recombination in mammalian cells between endogenous and introduced SV40 genomes. Cell 43, 695-703.

Jackson, E. L., Willis, N., Mercer, K., Bronson, R. T., Crowley, D., Montoya, R., Jacks, T., and Tuveson, D. A. (2001). Analysis of lung tumor initiation and progression using conditional expression of oncogenic K-ras. Genes & development 15, 3243-3248.

Jesien-Lewandowicz, E., Jesionek-Kupnicka, D., Zawlik, I., Szybka, M., Kulczycka-Wojdala, D., Rieske, P., Sieruta, M., Jaskolski, D., Och, W., Skowronski, W., et al. (2009). High incidence of MGMT promoter methylation in primary glioblastomas without correlation with TP53 gene mutations. Cancer genetics and cytogenetics 188, 77-82.

Ji, H., Ramsey, M. R., Hayes, D. N., Fan, C., McNamara, K., Kozlowski, P., Torrice, C., Wu, M. C., Shimamura, T., Perera, S. A., et al. (2007). LKB1 modulates lung cancer differentiation and metastasis. Nature 448, 807-810.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Johnson, L., Mercer, K., Greenbaum, D., Bronson, R. T., Crowley, D., Tuveson, D. A., and Jacks, T. (2001). Somatic activation of the K-ras oncogene causes early onset lung cancer in mice. Nature 410, 1111-1116.

Kaczmarczyk, G., Lewandowski, R., Trautsolt, W., Ziolkowski, A., and Kozielski, J. (2012). Cytological examination of pleural cavity lavage accompanied by the study of gene promoter hypermethylation of p16 and 06-methylguanine-DNA-methyltransferase genes in diagnostics of non-small cell lung cancer metastatic changes into pleura. Contemporary oncology 16, 322-327.

Kaina, B., Christmann, M., Naumann, S., and Roos, W. P. (2007). MGMT: key node in the battle against genotoxicity, carcinogenicity and apoptosis induced by alkylating agents. DNA repair 6, 1079-1099.

Kandoth, C., McLellan, M. D., Vandin, F., Ye, K., Niu, B., Lu, C., Xie, M., Zhang, Q., McMichael, J. F., Wyczalkowski, M. A., et al. (2013). Mutational landscape and significance across 12 major cancer types. Nature 502, 333-339.

Koboldt, D. C., Zhang, Q., Larson, D. E., Shen, D., McLellan, M. D., Lin, L., Miller, C. A., Mardis, E. R., Ding, L., and Wilson, R. K. (2012). VarScan 2: somatic mutation and copy number alteration discovery in cancer by exome sequencing. Genome research 22, 568-576.

Koike-Yusa, H., Li, Y., Tan, E. P., Velasco-Herrera Model, C., and Yusa, K. (2014). Genome-wide recessive genetic screening in mammalian cells with a lentiviral CRISPR-guide RNA library. Nature biotechnology 32, 267-273.

Kumar, M. S., Pester, R. E., Chen, C. Y., Lane, K., Chin, C., Lu, J., Kirsch, D. G., Golub, T. R., and Jacks, T. (2009). Dicer1 functions as a haploinsufficient tumor suppressor. Genes & development 23, 2700-2704.

Langmead, B., Trapnell, C., Pop, M., and Salzberg, S. L. (2009). Ultrafast and memory-efficient alignment of short DNA sequences to the human genome. Genome biology 10, R25.

Li, H., and Durbin, R. (2010). Fast and accurate long-read alignment with Burrows-Wheeler transform. Bioinformatics 26, 589-595.

Limberis, M. P., and Wilson, J. M. (2006). Adeno-associated virus serotype 9 vectors transduce murine alveolar and nasal epithelia and can be readministered. Proceedings of the National Academy of Sciences of the United States of America 103, 12993-12998.

Mali, P., Yang, L. H., Esvelt, K. M., Aach, J., Guell, M., DiCarlo, J. E., Norville, J. E., and Church, G. M. (2013). RNA-Guided Human Genome Engineering via Cas9. Science 339, 823-826.

Martin, M. (2011). Cutadapt removes adapter sequences from high-throughput sequencing reads. EMBnet 17, 1.

McClatchey, A. I., Saotome, I., Mercer, K., Crowley, D., Gusella, J. F., Bronson, R. T., and Jacks, T. (1998). Mice heterozygous for a mutation at the Nf2 tumor suppressor locus develop a range of highly metastatic tumors. Genes & development 12, 1121-1133.

McFadden, D. G., Papagiannakopoulos, T., Taylor-Weiner, A., Stewart, C., Carter, S. L., Cibulskis, K., Bhutkar, A., McKenna, A., Dooley, A., Vernon, A., et al. (2014). Genetic and clonal dissection of murine small cell lung carcinoma progression by genome sequencing. Cell 156, 1298-1311.

Mitzner, W., Brown, R., and Lee, W. (2001). In vivo measurement of lung volumes in mice. Physiological genomics 4, 215-221.

Molenaar, R. J., Verbaan, D., Lamba, S., Zanon, C., Jeuken, J. W., Boots-Sprenger, S. H., Wesseling, P., Hulsebos, T. J., Troost, D., van Tilborg, A. A., et al. (2014). The combination of IDH1 mutations and MGMT methylation status predicts survival in glioblastoma better than either IDH1 or MGMT alone. Neuro-oncology 16, 1263-1273.

Naba, A., Clauser, K. R., Lamar, J. M., Carr, S. A., and Hynes, R. O. (2014a). Extracellular matrix signatures of human mammary carcinoma identify novel metastasis promoters. eLife 3, e01308.

Naba, A., Clauser, K. R., Whittaker, C. A., Carr, S. A., Tanabe, K. K., and Hynes, R. O. (2014b). Extracellular matrix signatures of human primary metastatic colon cancers and their metastases to liver. BMC cancer 14, 518.

Nissen, L. J., Cao, R., Hedlund, E. M., Wang, Z., Zhao, X., Wetterskog, D., Funa, K., Brakenhielm, E., and Cao, Y. (2007). Angiogenic factors FGF2 and PDGF-BB synergistically promote murine tumor neovascularization and metastasis. The Journal of clinical investigation 117, 2766-2777.

Park, W. Y., Kim, M. H., Shin, D. H., Lee, J. H., Choi, K. U., Kim, J. Y., Park do, Y., Lee, C. H., and Sol, M. Y. (2012). Ciliated adenocarcinomas of the lung: a tumor of non-terminal respiratory unit origin. Modern pathology: an official journal of the United States and Canadian Academy of Pathology, Inc 25, 1265-1274.

Patel et al. (2014) Single-cell RNA-seq highlights intratumoral heterogeneity in primary glioblastoma. Science 344(6190):1396-1401.

Platt, R. J., Chen, S., Zhou, Y., Yim, M. J., Swiech, L., Kempton, H. R., Dahlman, J. E., Parnas, O., Eisenhaure, T. M., Jovanovic, M., et al. (2014). CRISPR-Cas9 Knockin Mice for Genome Editing and Cancer Modeling. Cell 159, 440-455.

Pylayeva-Gupta, Y., Grabocka, E., and Bar-Sagi, D. (2011). RAS oncogenes: weaving a tumorigenic web. Nature reviews Cancer 11, 761-774.

Sanjana, N. E., Shalem, O., and Zhang, F. (2014). Improved vectors and genome-wide libraries for CRISPR screening. Nature Methods 11, 783-784.

Schiano, C., Casamassimi, A., Rienzo, M., de Nigris, F., Sommese, L., and Napoli, C. (2014). Involvement of Mediator complex in malignancy. Biochimica et biophysica acta 1845, 66-83.

Schneider, C. A., Rasband, W. S., and Eliceiri, K. W. (2012). NIH Image to ImageJ: 25 years of image analysis. Nature methods 9, 671-675.

Shackelford, D. B., and Shaw, R. J. (2009). The LKB1-AMPK pathway: metabolism and growth control in tumour suppression. Nature reviews Cancer 9, 563-575.

Shalek et al. (2013) Single-cell transcriptomics reveals bimodality in expression and splicing in immune cells. Nature 498(7453):236-240.

Shalek et al. (2014) Single-cell RNA-seq reveals dynamic paracrine control of cellular variation. Nature 510(7505): 363-369.

Shalem, O., Sanjana, N. E., Hartenian, E., Shi, X., Scott, D. A., Mikkelsen, T. S., Heckl, D., Ebert, B. L., Root, D. E., Doench, J. G., et al. (2014). Genome-scale CRISPR-Cas9 knockout screening in human cells. Science 343, 84-87.

Tang, J. T., Wang, J. L., Du, W., Hong, J., Zhao, S. L., Wang, Y. C., Xiong, H., Chen, H. M., and Fang, J. Y. (2011). MicroRNA 345, a methylation-sensitive microRNA is involved in cell proliferation and invasion in human colorectal cancer. Carcinogenesis 32, 1207-1215.

Tano, K., Shiota, S., Collier, J., Foote, R. S., and Mitra, S. (1990). Isolation and structural characterization of a cDNA clone encoding the human DNA repair protein for O6-alkylguanine. Proceedings of the National Academy of Sciences of the United States of America 87, 686-690.

TCGA-Network (2012). Comprehensive genomic characterization of squamous cell lung cancers. Nature 489(7417): 519-25.

TCGA-Network (2014a). Comprehensive molecular characterization of urothelial bladder carcinoma. Nature 507, 315-322.

TCGA-Network (2014b). Comprehensive molecular profiling of lung adenocarcinoma. Nature Published online 9 Jul. 2014.

Teo, A. K., Oh, H. K., Ali, R. B., and Li, B. F. (2001). The modified human DNA repair enzyme O(6)-methylguanine-DNA methyltransferase is a negative regulator of estrogen receptor-mediated transcription upon alkylation DNA damage. Molecular and cellular biology 21, 7105-7114.

Vanharanta, S., and Massague, J. (2013). Origins of metastatic traits. Cancer cell 24, 410-421.

Waghorne, C., Thomas, M., Lagarde, A., Kerbel, R. S., and Breitman, M. L. (1988). Genetic evidence for progressive selection and overgrowth of primary tumors by metastatic cell subpopulations. Cancer research 48, 6109-6114.

Wang, T., Wei, J. J., Sabatini, D. M., and Lander, E. S. (2014). Genetic Screens in Human Cells Using the CRISPR-Cas9 System. Science 343, 80-84.

Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918.

Whittaker, S. R., Theurillat, J. P., Van Allen, E., Wagle, N., Hsiao, J., Cowley, G. S., Schadendorf, D., Root, D. E., and Garraway, L. A. (2013). A genome-scale RNA interference screen implicates NF1 loss in resistance to RAF inhibition. Cancer discovery 3, 350-362.

Xue, W., Chen, S., Yin, H., Tammela, T., Papagiannakopoulos, T., Joshi, N. S., Cai, W., Yang, G., Bronson, R., Crowley, D. G., et al. (2014). CRISPR-mediated direct mutation of cancer genes in the mouse liver. Nature.

Yokota, J., Nishioka, M., Tani, M., and Kohno, T. (2003). Genetic alterations responsible for metastatic phenotypes of lung cancer cells. Clinical & experimental metastasis 20, 189-193.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of recording a temporal ordering of a first and second cellular event comprising:
(a) providing a cell comprising a CRISPR-Cas system, said CRISPR-Cas system comprising:
(i) a first and a second guide RNA that target a first and a second recorder DNA sequence, and
(ii) a Cas protein capable of forming a complex with the first and the second guide RNAs and modifying the first and the second recorder DNA sequences,
wherein the first and second recorder DNA sequences are overlapping and modification of the first recorder DNA sequence by the Cas protein destroys a cut site of the second recorder DNA sequence, and
wherein the first guide RNA is encoded by a nucleic acid molecule operably connected in the cell with a regulatory element comprising an inducible promoter that is activated in parallel to the first cellular event or as a consequence of the first cellular event, and the second guide RNA is encoded by a nucleic acid molecule operably connected in the cell with a regulatory element comprising an inducible promoter that is activated in parallel to the second cellular event or as a consequence of the second cellular event; and
(b) detecting the temporal ordering of the cellular events based on detection of a modification of said first or second recorder DNA sequences.

2. The method according to claim 1, wherein the cellular event is a change in expression of a gene of interest, a change in level of a protein of interest, a change in the level of an intracellular molecule, a change in a posttranslational modification, a change in the activity of a factor of interest, a change in microenvironment, exposure to a molecule of interest, activation of a transcription factor, deactivation of a transcriptional repressor, recruitment of a transcription factor, activation of a signal transduction pathway, or remodeling of chromatin.

3. The method of claim 2, wherein exposure to a factor of interest comprises exposure to a chemical, biochemical, signaling molecule, or pathogen.

4. The method according to claim 2, wherein said first or second recorder DNA sequence is not comprised in said gene of interest.

5. The method according to claim 2, wherein said CRISPR-Cas system does not modify expression of said gene of interest.

6. The method according to claim 1, wherein the promoter is a promoter of a gene of interest.

7. The method according to claim 1, wherein the promoter is responsive to a transcription factor.

8. The method according to claim 7, wherein the transcription factor is recruited to the promoter as a result of activation of a signal transduction pathway and/or the promoter is responsive to a nuclear receptor.

9. The method according to claim 1, wherein said method further comprises introducing in said cell a vector comprising said recorder DNA sequences and said method comprises detection of the modification of said recorder DNA sequences on said vector.

10. The method according to claim 1, wherein said recorder DNA sequences are:
not endogenous to said cell; or
a sequence endogenous to said cell and selected based on impact of the modification of the recorder DNA sequence by the CRISPR-Cas system on the functioning of the cell.

11. The method according to claim 1, wherein said CRISPR-Cas system is multiplexed or self-inactivating.

12. The method according to claim 1, wherein the cell further comprises an additional first and second recorder DNA sequence that are not overlapping and are the same recorder sequences as the overlapping recorder sequences, wherein modifying the additional non-overlapping recorder sequences do not result in destruction of either recorder sequence, whereby each cellular event can additionally be recorded independent of temporal ordering.

13. The method according to claim 1, wherein said modification of said recorder DNA sequences comprises inducing one or more mutations in said DNA recorder sequences.

14. The method of claim 13, wherein the one or more mutations comprise one or more point mutations.

15. The method of claim 1, wherein the modification is detected by DNA sequencing, PCR, hybridization, RFLP, AFLP, single cell PCR, or single cell DNA or RNA sequencing.

16. The method according to claim 1, which further comprises introducing into said cell a nucleic acid molecule encoding one or more components of the CRISPR-Cas system.

17. The method according to claim 1, wherein said cell is a eukaryotic cell.

18. The method according to claim 1, wherein said guide RNAs, said Cas protein, or both are conditionally and/or inducibly expressed in said cell.

19. The method according to claim 1, wherein each of said guide RNAs comprises
a guide sequence, a tracr mate sequence and a tracr sequence; and/or
a single guide RNA.

20. The method according to claim 19, wherein said guide sequence and said tracr mate sequence are arranged in a 5' to 3' orientation on a single nucleic acid molecule.

21. The method according to claim 19, wherein said guide sequence, said tracr mate sequence, and said tracr sequence are arranged in a 5' to 3' orientation on a single nucleic acid molecule.

22. The method according to claim 19, wherein when transcribed, the tracr mate sequence hybridizes to the tracr sequence and the guide sequence directs sequence-specific binding of a CRISPR complex to the recorder DNA sequences,
wherein the CRISPR complex comprises the Cas protein complexed with (1) the guide sequence that is hybridized to the first or second recorder DNA sequence, and (2) the tracr mate sequence that is hybridized to the tracr sequence.

23. The method according to claim 19, wherein the guide RNAs; or the tracr sequence, tracr mate sequence, and guide sequence together, comprise two or more hairpins.

24. The method according to claim 1, wherein said guide RNAs, said Cas protein, or both are introduced into the cell by a delivery system comprising viral particles, liposomes, electroporation, microinjection or conjugation, or by means of transduction.

25. The method according to claim 1, wherein the Cas protein:
is codon optimized for expression in a eukaryotic cell;
is a type II Cas protein:
is a Cas protein originating from *Streptococcus pyogenes, Streptococcus thermophiles*, or *Staphylococcus aureus;*
is a mutated Cas having an altered catalytic activity;
is a mutated Cas having a nickase activity; and/or comprises at least one or more nuclear localization sequences (NLSs).

26. The method according to claim 1, wherein the method is conducted in vivo in a non-human organism or ex vivo on a cell taken from said organism, optionally wherein said cell is returned to said organism.

27. The method of claim 1, wherein the modification is detected by high throughput sequencing.

28. The method of claim 1, wherein the detection of the modification comprises detecting one or more variants of the recorder DNA sequences.

29. The method of claim 1, wherein the Cas protein is fused with a different protein.

30. The method of claim 1, wherein the Cas protein is under control of an inducible promoter.

31. The method of claim 1, wherein said CRISPR-Cas system is self-inactivating.

\* \* \* \* \*

UNITED STATES PATENT AND TRADEMARK OFFICE
CERTIFICATE OF CORRECTION

PATENT NO. : 11,643,669 B2
APPLICATION NO. : 15/837835
DATED : May 9, 2023
INVENTOR(S) : Alexander K. Shalek et al.

It is certified that error appears in the above-identified patent and that said Letters Patent is hereby corrected as shown below:

On the Title Page

Item (56), in Column 2, under "Other Publications", Line 10, delete "integrating" and insert -- Integrating --.

On the page 2, item (56), in Column 2, under "Other Publications", Line 2, delete "Ceils," and insert -- Cells, --.

On the page 2, item (56), in Column 2, under "Other Publications", Line 15, delete "Dong," and insert -- Cong, --.

On the page 3, item (56), in Column 1, under "Other Publications", Line 9, delete "Oct. 39," and insert -- Oct. 09, --.

In the Specification

In Column 30, Line 40, delete "CRISPRI" and insert -- CRISPR --.

In Column 30, Line 47, delete "CRISPRI" and insert -- CRISPR --.

In Column 32, Line 10, delete "CRISPRI." and insert -- CRISPR. --.

In Column 40, Line 67, delete "j-actin" and insert -- β-actin --.

In Column 42, Line 38, delete "lid" and insert -- 11d --.

In Column 48, Line 61 (Table 1), delete "Corynebacter" and insert -- Corynebacterium --.

In Column 50, Line 20, delete "100 l)" and insert -- 100 µl) --.

Signed and Sealed this
Sixteenth Day of April, 2024

Katherine Kelly Vidal
*Director of the United States Patent and Trademark Office*

SEQUENCE LISTING

```
<160> NUMBER OF SEQ ID NOS: 38

<210> SEQ ID NO 1
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 1
nnnnnnnnnn nnnnnnnnnn ngg                                            23

<210> SEQ ID NO 2
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 2
nnnnnnnnnn nnngg                                                     15

<210> SEQ ID NO 3
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
```

```
<221> NAME/KEY: modified_base
<222> LOCATION: (21)..(21)
<223> OTHER INFORMATION: a, c, t, g, unknown or other

<400> SEQUENCE: 3
nnnnnnnnnn nnnnnnnnnn ngg                                              23

<210> SEQ ID NO 4
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 4
nnnnnnnnnn nngg                                                        14

<210> SEQ ID NO 5
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 5
nnnnnnnnnn nnnnnnnnnn nnagaaw                                          27

<210> SEQ ID NO 6
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 6
nnnnnnnnnn nnnnagaaw                                                   19

<210> SEQ ID NO 7
<211> LENGTH: 27
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 7
nnnnnnnnnn nnnnnnnnnn nnagaaw                                              27

<210> SEQ ID NO 8
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 8
nnnnnnnnnn nnnagaaw                                                        18

<210> SEQ ID NO 9
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 9
nnnnnnnnnn nnnnnnnnnn nggng                                                25

<210> SEQ ID NO 10
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
```

```
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 10
nnnnnnnnnn nnggng                                                       17

<210> SEQ ID NO 11
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 11
nnnnnnnnnn nnnnnnnnnn nggng                                             25

<210> SEQ ID NO 12
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 12
nnnnnnnnnn nnggng                                                       16

<210> SEQ ID NO 13
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other
```

<400> SEQUENCE: 13
nnnnnnnnnn nnnnnnnnnn gttttttgtac tctcaagatt tagaaataaa tcttgcagaa       60
gctacaaaga taaggcttca tgccgaaatc aacaccctgt cattttatgg cagggtgttt      120
tcgttattta attttt                                                        137

<210> SEQ ID NO 14
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 14
nnnnnnnnnn nnnnnnnnnn gttttttgtac tctcagaaat gcagaagcta caaagataag       60
gcttcatgcc gaaatcaaca ccctgtcatt ttatggcagg gtgttttcgt tatttaattt      120
ttt                                                                      123

<210> SEQ ID NO 15
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 15
nnnnnnnnnn nnnnnnnnnn gttttttgtac tctcagaaat gcagaagcta caaagataag       60
gcttcatgcc gaaatcaaca ccctgtcatt ttatggcagg gtgtttttt                    110

<210> SEQ ID NO 16
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 16
nnnnnnnnnn nnnnnnnnnn gttttagagc tagaaatagc aagttaaaat aaggctagtc        60
cgttatcaac ttgaaaaagt ggcaccgagt cggtgctttt tt                           102

<210> SEQ ID NO 17
<211> LENGTH: 88
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 17
nnnnnnnnnn nnnnnnnnnn gttttagagc tagaaatagc aagttaaaat aaggctagtc      60
cgttatcaac ttgaaaaagt gttttttt                                        88

<210> SEQ ID NO 18
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 18
nnnnnnnnnn nnnnnnnnnn gttttagagc tagaaatagc aagttaaaat aaggctagtc      60
cgttatcatt tttttt                                                     76

<210> SEQ ID NO 19
<211> LENGTH: 7
<212> TYPE: PRT
<213> ORGANISM: Simian virus 40

<400> SEQUENCE: 19

Pro Lys Lys Lys Arg Lys Val
1               5

<210> SEQ ID NO 20
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 20

Lys Arg Pro Ala Ala Thr Lys Lys Ala Gly Gln Ala Lys Lys Lys Lys
1               5                   10                  15

<210> SEQ ID NO 21
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 21

Pro Ala Ala Lys Arg Val Lys Leu Asp
1               5

<210> SEQ ID NO 22
<211> LENGTH: 11
<212> TYPE: PRT
<213> ORGANISM: Unknown
```

```
<220> FEATURE:
<221> NAME/KEY: source
<223> OTHER INFORMATION: /note="Description of Unknown:
      C-myc NLS sequence"

<400> SEQUENCE: 22

Arg Gln Arg Arg Asn Glu Leu Lys Arg Ser Pro
1               5                   10

<210> SEQ ID NO 23
<211> LENGTH: 38
<212> TYPE: PRT
<213> ORGANISM: Homo sapiens

<400> SEQUENCE: 23

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 24
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 24

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 25
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T Protein sequence"

<400> SEQUENCE: 25

Val Ser Arg Lys Arg Pro Arg Pro
1               5

<210> SEQ ID NO 26
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T Protein sequence"

<400> SEQUENCE: 26

Pro Pro Lys Lys Ala Arg Glu Asp
1               5
```

```
<210> SEQ ID NO 27
<211> LENGTH: 8
<212> TYPE: PRT
<213> ORGANISM: Homo sapiens

<400> SEQUENCE: 27

Pro Gln Pro Lys Lys Lys Pro Leu
1               5

<210> SEQ ID NO 28
<211> LENGTH: 12
<212> TYPE: PRT
<213> ORGANISM: Mus musculus

<400> SEQUENCE: 28

Ser Ala Leu Ile Lys Lys Lys Lys Lys Met Ala Pro
1               5                   10

<210> SEQ ID NO 29
<211> LENGTH: 5
<212> TYPE: PRT
<213> ORGANISM: Influenza virus

<400> SEQUENCE: 29

Asp Arg Leu Arg Arg
1               5

<210> SEQ ID NO 30
<211> LENGTH: 7
<212> TYPE: PRT
<213> ORGANISM: Influenza virus

<400> SEQUENCE: 30

Pro Lys Gln Lys Lys Arg Lys
1               5

<210> SEQ ID NO 31
<211> LENGTH: 10
<212> TYPE: PRT
<213> ORGANISM: Hepatitis delta virus

<400> SEQUENCE: 31

Arg Lys Leu Lys Lys Lys Ile Lys Lys Leu
1               5                   10

<210> SEQ ID NO 32
<211> LENGTH: 10
<212> TYPE: PRT
<213> ORGANISM: Mus musculus

<400> SEQUENCE: 32

Arg Glu Lys Lys Lys Phe Leu Lys Arg Arg
1               5                   10

<210> SEQ ID NO 33
<211> LENGTH: 20
<212> TYPE: PRT
<213> ORGANISM: Homo sapiens

<400> SEQUENCE: 33

Lys Arg Lys Gly Asp Glu Val Asp Gly Val Asp Glu Val Ala Lys Lys
1               5                   10                  15

Lys Ser Lys Lys
            20
```

<210> SEQ ID NO 34
<211> LENGTH: 17
<212> TYPE: PRT
<213> ORGANISM: Homo sapiens

<400> SEQUENCE: 34

Arg Lys Cys Leu Gln Ala Gly Met Asn Leu Glu Ala Arg Lys Thr Lys
1               5                   10                  15

Lys

<210> SEQ ID NO 35
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
gatgtccaag ttcacaagac cagaccacta ctgaatataa ggtaggaaac tgttgaaatt      60
ccttgtttgt aattattatt                                                  80

<210> SEQ ID NO 36
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
aataataatt acaaacaagg aatttcaaca gtttcctacc ttatattcag tagtggtctg      60
gtcttgtgaa cttggacatc                                                  80

<210> SEQ ID NO 37
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
gatgtccaag ttcacaagac cagaccacga atataaggta ggaaactgtt gaaattcctt      60
gtttgtaatt attatt                                                      76

<210> SEQ ID NO 38
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
gatgtccaag ttcacaagac cagacctata aggtaggaaa ctgttgaaat tccttgtttg      60
taattattat t                                                           71